(12) United States Patent
Selinfreund

(10) Patent No.: US 6,232,124 B1
(45) Date of Patent: *May 15, 2001

(54) AUTOMATED FINGERPRINT METHODS AND CHEMISTRY FOR PRODUCT AUTHENTICATION AND MONITORING

(75) Inventor: Richard H. Selinfreund, Branford, CT (US)

(73) Assignee: Verification Technologies, Inc., Centerbrook, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/191,947

(22) Filed: Nov. 13, 1998

Related U.S. Application Data

(63) Continuation-in-part of application No. 08/969,194, filed on Nov. 13, 1997, now abandoned, which is a continuation-in-part of application No. 08/852,108, filed on May 6, 1997, now abandoned, which is a continuation-in-part of application No. 08/642,927, filed on May 6, 1996, now Pat. No. 5,753,511.

(51) Int. Cl.⁷ .................................................. G01N 21/64
(52) U.S. Cl. .............................. 436/20; 436/24; 436/172
(58) Field of Search ................................ 436/56, 20, 24, 436/22, 23, 2, 172

(56) References Cited

U.S. PATENT DOCUMENTS

| | | |
|---|---|---|
| D. 248,044 | 5/1978 | Odom et al. . |
| D. 414,272 | 9/1999 | O'Bear et al. . |
| 1,822,098 | 9/1931 | Huntress . |
| 2,265,198 | 12/1941 | Riley . |
| 2,521,124 | 9/1950 | Miller . |
| 3,356,462 | 12/1967 | Cooke et al. . |
| 3,412,245 | 11/1968 | Halverson . |
| 3,444,517 | 5/1969 | Rabinow . |
| 3,473,027 | 10/1969 | Freeman et al. . |
| 3,500,047 | 3/1970 | Berry . |
| 3,533,744 | 10/1970 | Unger . |
| 3,591,283 | 7/1971 | Peisach . |
| 3,624,644 | 11/1971 | Higgins . |
| 3,649,464 | 3/1972 | Freeman . |
| 3,662,181 | 5/1972 | Hercher et al. . |
| 3,663,813 | 5/1972 | Shaw . |
| 3,886,083 | 5/1975 | Laxer . |
| 3,928,226 | 12/1975 | McDonough et al. . |
| 3,992,158 | 11/1976 | Przybylowicz et al. . |
| 3,996,006 | 12/1976 | Pagano . |
| 4,015,131 | 3/1977 | McDonough et al. . |
| 4,018,643 | 4/1977 | Levine . |
| 4,038,151 | 7/1977 | Fadler et al. . |
| 4,053,433 | 10/1977 | Lee . |
| 4,077,845 | 3/1978 | Johnson . |
| 4,078,656 | 3/1978 | Crane et al. . |
| 4,087,332 | 5/1978 | Hansen . |
| 4,118,280 | 10/1978 | Charles et al. . |
| 4,146,792 | 3/1979 | Stenzel et al. . |
| 4,154,795 | 5/1979 | Thorne . |
| 4,202,491 | 5/1980 | Suzuki . |
| 4,235,964 | 11/1980 | Bochner . |
| 4,243,694 | 1/1981 | Mansukhani . |
| 4,260,392 | 4/1981 | Lee . |
| 4,329,317 | 5/1982 | Detweiler et al. . |
| 4,365,970 | 12/1982 | Lawrence et al. . |
| 4,382,064 | 5/1983 | Detweiler et al. . |
| 4,387,112 | 6/1983 | Blach . |
| 4,439,356 | 3/1984 | Khanna et al. . |
| 4,451,521 | 5/1984 | Kaule et al. . |
| 4,451,530 | 5/1984 | Kaule et al. . |
| 4,468,410 | 8/1984 | Zeya . |
| 4,485,308 | 11/1984 | Rabatin . |
| 4,486,536 | 12/1984 | Baker et al. . |

(List continued on next page.)

FOREIGN PATENT DOCUMENTS

| | | |
|---|---|---|
| 654467A5 | 2/1986 | (CH) . |
| 2 118 928 | 11/1971 | (DE) . |
| 196 17 106 A1 | 10/1997 | (DE) . |
| 0327163 | 9/1989 | (EP) . |
| 0589991B1 | 4/1994 | (EP) . |
| 0591315B1 | 4/1994 | (EP) . |
| 0 736 767 A1 | 10/1996 | (EP) . |
| 2 258 528 | 2/1993 | (GB) . |
| 2298713B | 9/1996 | (GB) . |
| 2 334 574 | 8/1999 | (GB) . |
| 63-184039 | 7/1988 | (JP) . |
| WO9506249 | 2/1995 | (WO) . |
| WO 97131332 | 8/1997 | (WO) . |

OTHER PUBLICATIONS

Eric V. Anslyn, et al. "Rapid and Efficient Analysis of Multiple Chemical/Biochemical Agents in Solution Using Sensor Arrays: Toward the Development of an Electronic Tongue," The University of Texas at Austin.

Junior LB 9509, the portable luminometer:, downloaded from http://www.berthold.com.au/bioanalytical_pages/LB9509.html, downloaded Oct. 26, 1999.

The Invisible Barcode, downloaded from http://www.canadianpackaging.com/C... aging, downloaded Jul. 1999 1999.

1st Advanced Packaging Technology Conference held Nov. 9–11, 1998, downloaded from http://auburn.main.com/tse/imi/completed/advanced–pkg–euro.html; downloaded Jul. 1999.

(List continued on next page.)

Primary Examiner—Jeffrey Snay
(74) Attorney, Agent, or Firm—Wolf, Greenfield & Sacks, P.C.

(57) ABSTRACT

Highly efficient, low cost, methods and compounds to determine product authenticity, tampering, manufacturing compliance are provided. The methods and chemicals defined are capable of measuring the relative amounts of key materials in these products. The compounds are light emitting and interact with key elements in products like, neutral spirits, vodka, tequila, soft drinks and infant formulas. After the interactions are complete, methods are employed to determine resulting key components by light emission.

16 Claims, 3 Drawing Sheets

U.S. PATENT DOCUMENTS

| | | |
|---|---|---|
| 4,501,496 | 2/1985 | Griffin . |
| 4,514,085 | 4/1985 | Kaye . |
| 4,540,595 | 9/1985 | Acitelli et al. . |
| 4,557,900 | 12/1985 | Heitzmann . |
| 4,567,370 | 1/1986 | Falls . |
| 4,589,551 | 5/1986 | Hellon . |
| 4,589,743 | 5/1986 | Clegg . |
| 4,598,205 | 7/1986 | Kaule et al. . |
| 4,620,776 | 11/1986 | Ima . |
| 4,631,174 | 12/1986 | Kondo . |
| 4,632,901 | 12/1986 | Valkirs et al. . |
| 4,642,526 | 2/1987 | Hopkins . |
| 4,736,425 | 4/1988 | Jalon . |
| 4,746,631 | 5/1988 | Clagett . |
| 4,756,557 | 7/1988 | Kaule et al. . |
| 4,767,205 | 8/1988 | Schwartz et al. . |
| 4,789,804 | 12/1988 | Karube et al. . |
| 4,806,316 | 2/1989 | Johnson et al. . |
| 4,818,677 | 4/1989 | Hay-Kaufman et al. . |
| 4,865,812 | 9/1989 | Kuntz et al. . |
| 4,882,195 | 11/1989 | Butland . |
| 4,889,365 | 12/1989 | Chouinard . |
| 4,897,173 | 1/1990 | Nankai et al. . |
| 4,921,280 | 5/1990 | Jalon . |
| 4,927,180 | 5/1990 | Trundle et al. . |
| 4,948,442 | 8/1990 | Manns . |
| 4,966,856 | 10/1990 | Ito et al. . |
| 4,983,817 | 1/1991 | Dolash et al. . |
| 5,005,873 | 4/1991 | West . |
| 5,018,866 | 5/1991 | Osten . |
| 5,030,421 | 7/1991 | Muller . |
| 5,030,832 | 7/1991 | Williams et al. . |
| 5,047,215 | 9/1991 | Manns . |
| 5,049,673 | 9/1991 | Tsien et al. . |
| 5,093,147 | 3/1992 | Andrus et al. . |
| 5,106,582 | 4/1992 | Baker . |
| 5,118,349 | 6/1992 | Jalon . |
| 5,128,243 | 7/1992 | Potter et al. . |
| 5,128,882 | 7/1992 | Cooper et al. . |
| 5,135,569 | 8/1992 | Mathias . |
| 5,139,812 | 8/1992 | Lebacq . |
| 5,147,042 | 9/1992 | Levy . |
| 5,176,257 | 1/1993 | Levy . |
| 5,194,289 | 3/1993 | Butland . |
| 5,200,051 | 4/1993 | Cozzette et al. . |
| 5,208,630 | 5/1993 | Goodbrand et al. . |
| 5,246,869 | 9/1993 | Potter et al. . |
| 5,260,032 | 11/1993 | Muller . |
| 5,264,103 | 11/1993 | Yoshioka et al. . |
| 5,272,090 | 12/1993 | Gavish et al. . |
| 5,279,967 | 1/1994 | Bode . |
| 5,282,894 | 2/1994 | Albert et al. . |
| 5,286,286 | 2/1994 | Winnik et al. . |
| 5,292,000 | 3/1994 | Levy . |
| 5,292,855 | 3/1994 | Krutak et al. . |
| 5,313,264 | 5/1994 | Ivarsson et al. . |
| 5,319,436 | 6/1994 | Manns et al. . |
| 5,321,261 | 6/1994 | Valenta . |
| 5,336,714 | 8/1994 | Krutak et al. . |
| 5,338,066 | 8/1994 | Gundjian . |
| 5,338,067 | 8/1994 | Gundjian . |
| 5,360,628 | 11/1994 | Butland . |
| 5,366,902 | 11/1994 | Cox et al. . |
| 5,409,583 | 4/1995 | Yoshioka et al. . |
| 5,409,666 | 4/1995 | Nagel et al. . |
| 5,418,855 | 5/1995 | Liang et al. . |
| 5,421,869 | 6/1995 | Gundjian et al. . |
| 5,424,959 * | 6/1995 | Reyes et al. .......................... 364/498 |
| 5,429,952 * | 7/1995 | Garner et al. .......................... 436/518 |
| 5,438,403 | 8/1995 | Hoshino et al. . |
| 5,450,190 | 9/1995 | Schwartz et al. . |
| 5,457,527 | 10/1995 | Manns et al. . |
| 5,494,638 | 2/1996 | Gullick . |
| 5,496,701 | 3/1996 | Pollard-Knight . |
| 5,498,549 | 3/1996 | Nagel et al. . |
| 5,516,362 | 5/1996 | Gundjian et al. . |
| 5,521,984 | 5/1996 | Denenberg et al. . |
| 5,525,516 | 6/1996 | Krutak et al. . |
| 5,545,567 | 8/1996 | Gretillat et al. . |
| 5,547,501 | 8/1996 | Maruyama et al. . |
| 5,568,177 | 10/1996 | Talvalkar et al. . |
| 5,569,317 | 10/1996 | Sarada et al. . |
| 5,569,842 * | 10/1996 | Silvestri .............................. 73/53.05 |
| 5,574,790 | 11/1996 | Liang et al. . |
| 5,582,697 | 12/1996 | Ikeda et al. . |
| 5,589,350 | 12/1996 | Bochner . |
| 5,599,578 | 2/1997 | Butland . |
| 5,608,225 | 3/1997 | Kamimura et al. . |
| 5,611,433 | 3/1997 | Levy . |
| 5,614,008 | 3/1997 | Escano et al. . |
| 5,618,682 | 4/1997 | Scheirer . |
| 5,625,706 | 4/1997 | Lee et al. . |
| 5,631,170 | 5/1997 | Attridge . |
| 5,632,959 | 5/1997 | Mohajer . |
| 5,641,640 | 6/1997 | Hanning . |
| 5,650,062 | 7/1997 | Ikeda et al. . |
| 5,651,869 | 7/1997 | Yoshioka et al. . |
| 5,665,151 | 9/1997 | Escano et al. . |
| 5,671,288 | 9/1997 | Wilhelm et al. . |
| 5,673,338 | 9/1997 | Denenberg et al. . |
| 5,710,626 | 1/1998 | O'Rourke et al. . |
| 5,711,915 | 1/1998 | Siegmund et al. . |
| 5,716,825 | 2/1998 | Hancock et al. . |
| 5,719,948 | 2/1998 | Liang . |
| 5,728,350 | 3/1998 | Kinoshita et al. . |
| 5,736,342 | 4/1998 | Van Wie et al. . |
| 5,753,511 | 5/1998 | Selinfreund . |
| 5,762,873 | 6/1998 | Fanning et al. . |
| 5,773,808 | 6/1998 | Laser . |
| 5,774,160 | 6/1998 | Gundjian . |
| 5,776,713 | 7/1998 | Garner et al. . |
| 5,784,193 | 7/1998 | Ferguson . |
| 5,786,182 | 7/1998 | Catanzariti et al. . |
| 5,786,509 | 7/1998 | Belding et al. . |
| 5,800,785 | 9/1998 | Bochner . |
| 5,807,625 | 9/1998 | Amon et al. . |
| 5,811,152 | 9/1998 | Cleary . |
| 5,818,582 | 10/1998 | Fernandez et al. . |
| 5,822,473 | 10/1998 | Magel et al. . |
| 5,837,042 | 11/1998 | Lent et al. . |
| 5,851,489 | 12/1998 | Wolf et al. . |
| 5,856,174 | 1/1999 | Lipshutz et al. . |
| 5,861,618 | 1/1999 | Berson . |
| 5,867,586 | 2/1999 | Liang . |
| 5,874,219 | 2/1999 | Rava et al. . |
| 5,919,712 | 7/1999 | Herron et al. . |
| 5,922,188 | 7/1999 | Ikeda et al. . |
| 5,922,550 | 7/1999 | Everhart et al. . |
| 5,922,591 | 7/1999 | Anderson et al. . |
| 5,922,594 | 7/1999 | Löfås . |
| 5,923,413 | 7/1999 | Laskowski . |
| 5,927,547 | 7/1999 | Papen et al. . |
| 5,939,024 | 8/1999 | Robertson . |
| 5,955,352 | 9/1999 | Inoue et al. . |
| 5,955,729 | 9/1999 | Nelson et al. . |
| 5,961,926 | 10/1999 | Kolb et al. . |
| 5,989,835 | 11/1999 | Dunlay et al. . |
| 5,998,128 | 12/1999 | Roelant . |
| 6,001,573 | 12/1999 | Roelant . |

OTHER PUBLICATIONS

Phosphor Technology, downloaded from http:/www.phosphor.demon.co.uk/iruv.htm; downloaded Jul. 1999.

Fluorescent Inks downloaded from http://www.uvp.com/html/inks.html; downloaded Jul. 1999.

V.L. Engineering, Our Products; downloaded from http://www.vlengineering.com/products/wizard_PV6A Downloaded Jul. 1999.

R. Service, Microchip Arrays Put DNA on the Spot, Oct. 16, 1998, vol. 282 Science, pp. 396–399.

R. Service, Coming Soon: The Picket DNA Sequencer, Oct. 16, 1998, vol. 282, Science, pp. 399–401 402.

I, Amato, Fomenting a Revolution, in Miniature, Oct. 16, 1998, vol. 282, Science, pp. 402–404.

Web Site Disclosure: Packard Instrument Company: Tools for Life Science Research, pp. 1–2.

Bock, G., et al., "Photometric Analysis fo Antifading Reagents for Immunofluorescence with Laser and Conventional Illumination Sources," Journal of Histochemistry and Cytochemistry, 33: 699–705 (1985).

Crossley et al., Journal of the Chemical Society, Perkin Transactions 2, 1615 (1994).

Furomoto et al., IEEE, J. Quantum Electron, QE–6, 262 (1970).

Gill, D., "Inhibition of fading in fluorescence microscopy of fixed cells," Dept. of Physics, Ben Gurion University, Israel (Jul. 1978).

Huff, J., "Enhancement of Specific Immunofluorescent Findings with Use of a Para–Phenylenediamine Mounting Buffer," Journal of Investigative Dermatology, 78: 449–450 (1982).

Iatridou, H., et al., Cell Calcium, vol. 15, pp. 190–198, 1994.

Johnson, G.D., et al., "Fading of Immunofluorescence during Microscopy: a Study of the Phenomenon and its Remedy," Journal of Immunological Methods, 55: 231–242 (1982).

Johnson, G.D., et al., "A Simple Method of Reducing the Fading of Immunofluorescence During Microscopy," Journal of Immunological Methods, 43: 349–350 (1981).

Larsen, R., et al., "Spectroscopic and Molecular Modeling Studies of Caffeine Complexes with DNA Intercalators," Biophysical Journal, 70:443–452 (Jan. 1996).

Lee, S.P., et al., "A Fluorometric Assay for DNA Cleavage Reactions Characterized with BamH1 Restriction Endonuclease," Analytical Biochemistry, 220: 377–383 (1994).

Platt, J. L., et al., "Retardation of Fading and Enhancement of Intensity of Immunofluorescence by p–Phenylenediamine," Journal of Histochemistry and Cytochemistry, 31:840–842 (1983).

Stryer, L., "Fluorescence Energy Transfer as a Spectroscopic Ruler," Ann. Rev. Biochem., 47:819–46 (1978).

Uchiyama, H., et al., "Detection of Undegraded Oligonucleotides in Vivo Fluorescence Resonance Energy Transfer," Journal of Biological Chemistry, 271: 380–384, Jan. 1996).

Wittwer, C.T., et al., "Continuous Fluorescence Monitoring of Rapid Cycle DNA Amplification," BioTechniques, 22:130–138 (Jan. 1997).

Constant, et al., ACS Abstract, Issue of Chemical and Engineering News, Aug. 25, 1994.

Minata, et al., J. Biol. Chem. 264:8171 (1989).

AOAC Official Methods of Analysis, 1900, pp. 752–754.

Practical Fluorescence, Second Edition, G.G. Guilbault, Editor, Marcel Dekker, Inc. 1990 (p. 32).

Dragoco Report, 1990, pp. 12–13.

Chan, et al., Biochem. Biophys. Acta 204:252, 1970.

Raybourne, R.R., Flow Cytomety in Food Microbiology, FDA 1996, IFT Symposium (Jun. 21–22, 1996).

Barrett, T.J., Molecular Fingerprinting of Food Bourne Pathogens, CDD IFT Symposium, (Jun. 21–22, 1996).

Coons, et al., J. Exp. Med. 91:1–14 (1950).

Glabe, et al., Anal. Biochem. 130:287–294 (1983).

Biocode product literature, "Covert Product Identification".

Freemantle, M., "Downsizing Chemistry: Chemical analysis and synthesis on micriships promise a variety of potential benefits", C&EN London, pp. 27–36, Feb. 22, 1999.

Furneaux, R.C., et al., "The formation of controlled–porosity membranes from anodically oxidized aluminum", Nature, vol. 337, No. 6203, pp. 147–149, Jan. 12, 1989.

Schauer, C.L., et al., "Cross–reactive optical sensor arrays", ACS Meetings, San Francisco National Meeting, Downloaded from http://schedule.acs.org/cgi–bin/ACSperso. . . , Mar. 7, 2000.

Skolnick, A., "Russian and US Researchers Develop 'Biochips' for Faster, Inexpensive Biomedical Tests", JAMA, vol. 275, No. 8, pp. 581–582, Feb. 28, 1996.

Stanley, D., "UT scientists engineer a tiny arbiter of taste", Austin American Statesman Newspaper, p. B1, Jul. 26, 1998.

Stringer, "Photonics Center launches three new companies", Mass. High Tech., p. 11, Apr. 26–May 2, 1999.

Biacore Website, "Sensor chips for Biacore analysis systems", downloaded from webmaster.bia@eu.biacore.com; undated.

Biacore Website, "Principles of BIAtechnology", downloaded from webmaster.bia@eu.biacore.com, Undated.

Packard Website, "The Biochip Arrayer", downloaded from www.packardinst.com/prod_serv/–Biochiparrayer.htm, Oct. 26, 1999.

* cited by examiner

COMPOUND 1

COMPOUND 2

COMPOUND 3

COMPOUND 4

COMPOUND 5

AUTOMATED FINGERPRINT METHODS AND CHEMISTRY FOR PRODUCT AUTHENTICATION AND MONITORING

This application is a continuation-in-part of Ser. No. 08/969,194 filed Nov. 13, 1997, now abandoned, which is a continuation-in-part of Ser. No. 08/852,108 filed May 6, 1997, now abandoned, which is a continuation-in-part of Ser. No. 08/642,927, filed May 6, 1996, now U.S. Pat. No. 5,753,511 all for AUTOMATED FINGERPRINT METHODS AND CHEMISTRY FOR PRODUCT AUTHENTICATION AND MONITORING.

BACKGROUND OF THE INVENTION

This invention is in the general field of methods, reagents, and apparatus for authenticating or monitoring sample composition.

Authenticating and monitoring products to discriminate between very similar complex mixtures is useful for various reasons. First, the use of counterfeit substances (e.g., misbranded material from a competitor or misformulated material from a licensee/franchisee) should be detected to preserve the integrity of a brand.

Characteristics of a product can be used to identify its lot. Similar methods can be used in quality control tests. Also, product counterfeiting raises serious health and safety issues. In 1995, a counterfeit-labeled version of infant formula reportedly was distributed to 15 states in the continental United States. Counterfeit wine, spirits, perfume, infant formula, soft drinks, cosmetics, and pharmaceuticals are estimated to cost United States businesses 200 billion dollars per year ("The Boston Phoenix," Section One, Dec., 2, 1994).

It is important to develop rapid, cost effective, and enforceable methods to identify fraudulent or tampered products. It is also important to determine manufacturing compliance using automated methods to decrease the amount of time spent identifying fraudulent products. It is desirable to minimize the time required from highly skilled researchers and technicians to conduct and record the results of on-line, off-line, and off-the-shelf product authenticity/compliance tests.

There have been attempts to determine product (e.g., infant formula) authenticity by protein electrophoresis, which requires substantial time (and expense) for set up and analysis. In other industries, e.g. wine and spirits, Fourier-transform infrared analysis, gas chromatography, pH, Raman spectroscopy and other analytical methods have been used or proposed for product authentication (Constant et al., Differentiation of Alcoholic Beverages FT-IR Spectra. An Original Multivariate Approach, ACS Abstract presented at 208th ACS National Meeting, Aug. 25, 1994, published in the Issue of Chemical and Engineering News, 10 1994).

Biocode, Limited has used fluorescent labeled antibodies to determine ingredients in products.

U.S. Pat. No. 5,429,952 discloses adding light-emissive chemicals to a product for analysis, as exogenous product tags which do not ordinarily form part of the product.

The use of standard analytical methods to monitor every lot or batch for a product or competitor product for authenticity or compliance with laboratory equipment can often be costly.

SUMMARY OF THE INVENTION

I have discovered an automated method of developing a database to store information for "fingerprint"-type analysis of products (even as to product lot numbers and batch). The automated analysis is a method of evaluating and discriminating products, even within a narrow field or industry, competing and otherwise, e.g., to establish authenticity or point of origin of the product. The invention relates to a method for identifying analytes such as key ingredients and/or the relative amounts of analytes such as key ingredients in products. The method allows for authenticating and monitoring products for fraud and quality control using light emission. The invention also relates to light-emissive-compounds (e.g., including one or more light emissive compounds) which can be used to identify and quantitate the relative amounts of analytes in products.

In general, the methods pertain to obtaining an emission profile of a sample. An "emission profile", as used herein, refers to data collected relating to emission, for example, emission intensity or time of emission. The data collected for the emission profile can be expressed in relative terms, e.g. relative emission intensity or time of relative emission, when data for the sample and a standard and/or a control are compared.

In one aspect, the invention features a method for determining relatedness of a sample to a standard known to be authentic or known to have at least one selected characteristic of authentic material. The method includes: a) providing a mixture of sample and least one light-emissive compound ("LEC"); (b) irradiating the sample mixture with an irradiating wavelength of light; (c) monitoring at least one emitted wavelength of light (generated in response to the irradiating) to establish a sample emission profile; and (d) providing a standard fingerprint characteristic of a standard mixture; and (e) comparing the sample emission profile with the standard fingerprint to determine whether the sample is authentic. The standard mixture includes the standard and the light-emissive compound. The standard fingerprint is generated by irradiating several of the standard mixture with the irradiating wavelength and monitoring the emitted wavelength in response thereto.

In preferred embodiments, two and preferably three or more light-emissive compounds are employed, and a fingerprint profile of several light-emissive compounds is compared to the corresponding emission intensities for the sample. Most preferably, the light-emissive compounds emit light at nonoverlapping wave lengths, whereby multiple compounds can be added to the sample and/or standard at the same time.

In preferred embodiments, the method further includes: providing a background control mixture which includes the light-emissive compound without the sample or the standard; irradiating the background control mixture with the irradiating wavelength and monitoring the emitted wavelength in response thereto, to establish background emission; and determining the emission profile of the sample based on at least one difference between the emission of the control mixture and the emission of the sample mixture. It is preferred that the standard be a composition having a predetermined relative amount of a component characteristic of authentic material. The sample fingerprint is generated based on a first change in emission, determined by comparing the background emission and the emission from the sample mixture. The standard fingerprint is generated based on a second change in emissions, determined by comparing the background emission and the standard emission for each measurement. The comparing step includes comparing the first change in emission to the background adjusted fingerprint, e.g., to quantify relative amounts of sample component.

In another aspect of the invention, a method is provided for determining whether a product is authentic. A liquid sample of a test product is obtained and a light emissive compound then is added to the liquid sample to form a test sample. The light emissive compound interacts with an analyte of the product. The test sample is irradiated, and the intensity of light emitted from the test sample at a wavelength is determined. The intensity of light emitted from the test sample at this wavelength then is compared to the intensity of light emitted at the wavelength as a result of irradiating a mixture of the light emitting compound and an authentic liquid standard of the product, wherein similarity of light emission intensity is determinative of authenticity of the sample and this similarity of light emission intensity is determinative of nonauthenticity of the sample. In one important embodiment, the intensity of light emitted from the test sample is compared to the intensity of light emitted from a plurality of the mixture, and wherein authenticity requires the intensity of light emitted from the test sample to be within a pre-selected confidence limit defining a range of intensity calculated from the intensity of light emitted from the plurality of said mixture. The plurality of said mixture is at least four standards containing a mixture of the light emitting compound and an authentic liquid standard of the product, and preferably is four such mixtures.

In certain of the foregoing embodiments, the chemical composition of the product is unknown. In other of the embodiments, the chemical structure of the analyte to which the light emitting compound binds is unknown. In still other embodiments, the analyte is other than an exogenous product tag. In one particularly important embodiment, the product is a liquid consumable product.

As mentioned above, a plurality of light emissive compounds can be used. In such embodiments, it is preferred that each light emitting compound binds to a different analyte of the product. Most preferably, the light emissive compounds is a fluorescent dye.

In other preferred embodiments, the light-emissive compound is added to the sample by an automated pipette. It is preferred that the sample mixture be dispensed by an automated pipette in a multiwell plate.

In other preferred embodiments, the standard, the sample, or both, inherently include a fluorescent, phosphorescent, or luminescent compound. In some products the compound is caffeine.

In other preferred embodiments, the light-emissive compound is fluorescent, phosphorescent, or luminescent, and emission varies in response to quantity or quality of product analytes. Preferably, the light-emissive compound interacts with components of the sample, the standard, or both, to yield at least one fluorescent, phosphorescent, or luminescent component.

In other preferred embodiments, the standard is a composition having a predetermined relative amount of an analyte characteristic of authentic material, and the comparing step includes quantifying the relative amounts of the analyte in the sample.

In preferred embodiments, the method includes performing steps (b)–(c) described above, at least two times and preferably three times. Steps (b)–(c) may be performed using the same or different light-emissive compounds, and the same or different irradiating and emission wavelengths are monitored in each performed step.

In one important embodiment, the standard is a caffeine-containing beverage, and the light-emissive compound is: a) 5-(2-carbohydrazinomethylthioacetyl)aminofluorescein; b) 5-(4,6-dichlorotriazinyl)aminofluorescein; c)Fluo-3 pentaammonium salt (Minta et al., J. Biol. Chem. 264:8171, 1989 and U.S. Pat. No. 5,049,673); d) 4-aminofluorescein; e) 5-aminofluorescein; f) sulfite blue coumarin; g) courmarin diacid cryptand (CD222) (Costlei et al., J. of Chem. Society Perkins translation 2, p. 1615); or h) Eosin Y.

In another important embodiment, the standard is an infant formula, and the light-emissive compound is selected from the group consisting of 5-(2-carbohydrazinomethylthioacetyl) aminofluorescein, 5-(4,6-dichlorotriazinyl)aminofluorescein, Fluo-3 pentaammonium salt, or Courmarin benzothiazole, tetrapotassium salt (BTC5N) (Cell Calcium, p. 190, 1994). In other preferred embodiments, the standard contains corn syrup, and the light-emissive compound is selected from the group consisting of 5-(2-carbohydrazinomethylthioacetyl) aminofluorescein, 5-(4,6-dichlorotriazinyl) aminofluorescein, Fluo-3 pentaammonium salt, 4-aminofluorescein, 5-aminofluorescein, sulfite blue coumarin, courmarin diacid cryptand (CD222), or Eosin Y. In other preferred embodiments, the standard is an ethanol-containing beverage and the light-emissive compound is selected from the group consisting of 5-(2-carbohydrazinomethylthioacetyl)aminofluorescein, 5-(4,6-dichlorotriazinyl)aminofluorescein, Fluo-3 pentaammonium salt, proflavine hemisulfate, tetra(tetramethylammonium) salt, acridine orange hydrochloride hydrate, BTC-5N, acriflavine, 4-aminofluorescein, or 5-aminofluorescein. Compound 11 is sulfate blue coumarin. Compound 12 is courmarin diacid cryptand (CD222). Compound 13 is Eosin Y. In other preferred embodiments, the standard is an aqueous mixture, and the light-emissive compound is a compound that interacts or reacts with heavy metals, the light-emissive compound being selected from the group consisting of Fluo-3 pentaammonium salt, or BTC-5N.

In another aspect, the invention features a method for determining relatedness of a first sample to a second sample, neither of which is a known standard. The method includes: (a) providing a first sample mixture including the first sample and at least one light-emissive compound; (b) irradiating a plurality of the first sample mixture with an irradiating wavelength of light; (c) monitoring at least one emitted wavelength of light generated in response to the irradiating, to establish a first sample fingerprint characteristic of the first sample mixture; (d) providing a second sample fingerprint characteristic of a second sample mixture, the second sample mixture including the second sample and the light-emissive compound; the second sample fingerprint being generated by irradiating a plurality of the second sample mixture with the irradiating wavelength and monitoring the emitted wavelength in response thereto; and (e) comparing the first sample fingerprint with the second sample fingerprint to determine relatedness of the two samples.

In preferred embodiments, the first sample is identified as a specific product or as part of a homogeneous lot of a product by comparing the fingerprint profile or emission profile of the first sample to a library of fingerprints of samples whose product composition or lot number are known.

In other preferred embodiments, the method further includes providing one or more additional fingerprints to generate a fingerprint profile for each of at least two additional light emissive compounds and comparing the first sample mixture fingerprint profile to the second sample or standard fingerprint profile.

In preferred embodiments, the method is used to determine product authenticity, product tampering or product manufacturing compliance. In other preferred embodiments, the sample is a perfume, fragrance, flavor, food, or beverage product.

In another aspect of the invention, a method is provided for selecting a dye for determining authenticity of a product. A candidate dye is added to a plurality of candidate dilutions of a liquid sample of an authentic standard of the product, the candidate dye being light emissive at a particular wavelength when irradiated if it interacts with an analyte in the liquid sample. A test dilution then is selected at which the candidate dye emits light at a selected intensity when said candidate dye is added to said liquid sample at the test dilution. A range of intensity of light emission at discrete wavelengths is determined for a plurality of mixtures of said candidate dye and said liquid sample at said test dilution. An experimental intensity of light emission at the discrete wavelengths is then determined for a mixture of said candidate dye and a liquid sample of nonauthentic product at said test dilution. Finally, the experimental intensity at the discrete wavelengths is compared to the range of intensity of light emission at the discrete wavelengths, said dye being selected as useful for determining authenticity of said product if said experimental intensity falls outside of said range of light emission at the discrete wavelengths. In one embodiment, the candidate dye is a plurality of candidate dyes, each of the dyes emitting light at different wavelengths, and wherein the analyte is a plurality of analytes, each dye binding to a different of said plurality of the plurality of analytes. In an important embodiment, the chemical composition of the product is unknown and/or the chemical structure of the analyte is unknown. In other important embodiments, the product is a liquid consumable product.

In another aspect of the invention, a computer implemented method for determining authenticity of a liquid product is provided. The method involves receiving light emission data produced by adding a component to a test sample of the liquid product and measuring light emission therefrom. It also involves receiving light emission data produced by measuring light emission from a sample of a mixture of an authentic liquid product and the component. There then is a comparison of the intensity of light emission from the test sample to intensity of light emission from samples of the plurality of the mixtures, wherein authenticity requires the intensity of light emission from the test sample to be within a preselected confidence limit defining a range of intensity at discrete wavelengths calculated from the intensity of light emission at the discrete wavelengths from the plurality of the mixtures.

In one important embodiment, a computer database is used for storing and making available information about light emission of an authentic product. The database includes a computer-readable medium having a computer-readable logic stored thereon, wherein the computer-readable logic comprises a plurality of records for the authentic product indicating measurements of intensity of light emitted by samples of a plurality of mixtures of the authentic product with a component. The database also includes an indication of the component, wherein the records are accessible using an indication of the component and/or the authentic product wherein the step of receiving light emission data for the authentic product includes the step of accessing the computer-readable medium using an indication of the component and/or the product to retrieve the records.

In another aspect of the invention, a computer database for storing and making available information about light emission of an authentic product is provided. The database included a computer-readable medium having computer-readable logics stored thereon, wherein the computer-readable logic comprises a plurality of records for the authentic product indicating measurements of intensity of light emitted by samples of a plurality of mixtures of the authentic product with a component, and an indication of the component. Also included are means for accessing the computer-readable medium using an indication of the component and/or the authentic product to retrieve the records.

It is a feature also of the present invention that, when adding a light-emitting compound to a sample in accordance with the methods described herein, the sample can be separate from the standard. This differs from the situation where product tags are used, in that product tags are added to an authentic product to form a tagged mixture wherein the addition of the tag to the sample is not separate from the addition of the tag to the standard.

Light-emissive compounds are involved in light emission in response to irradiation with light of a different wavelength. Light emission of interest can be a result of phosphorescence, chemiluminescence, or, more preferably, fluorescence or polarized fluorescence. Specifically, the term "light emissive compounds," as used herein, means compounds that have one or more of the following properties: 1) they are a fluorescent, phosphorescent, or luminescent; 2) interact with components of the sample or the standard or both to yield at least one fluorescent, phosphorescent, or luminescent compound; or 3) interact with at least one fluorescent, phosphorescent, or luminescent compound in the sample, the standard, or both to alter emission at the emission wavelength. The emission wavelength can be any detectable wavelength including visible, infrared (including near infrared), and ultraviolet. Light, as used herein, likewise can be of any wavelength.

Light-emissive compounds also include compounds that cause, or interact with components of the standard or sample to cause, or alter, Raman Scatter at a scatter or emission wavelength. The Raman effect occurs when light from a strong source (typically a laser) interacts with a material. Most of the light is absorbed or scattered without wavelength change but some of the light is scattered into other wavelengths (the Raman scatter).

"Fingerprint" refers to the data set of light emission intensity from a light-emissive compound in combination with a liquid sample of a product measured at least three times, three such combinations measured at least once, or both. Accordingly, each product can have a particular fingerprint A "fingerprint profile" is an assembly of fingerprints of a liquid sample of a product in combination with a series (or profile) of different light-emissive compounds.

As noted above, the emission profile can include, but is not limited to, emission intensity and time of relative emission. The same information that can be derived about the amount and/or concentration of analytes by emission intensity measurement also can be derived from measurement of the time of emission, e.g. the time of relative emission of fluorescent compounds in a sample. Analysis of the emission intensity or time of relative emission can be done as described herein and by other methods known to one of ordinary skill in the art. Other emission properties measurable by one of ordinary skill in the art (e.g. emission half-life, emission decay characteristics) are also embraced in the term emission profile.

The term "analyte", as used herein, means a key ingredient or trace compound of the product. A native analyte is one which is ordinarily found in the unadulterated product, not added as an exogenous product tag. The invention relies upon interaction of light emissive compounds with such analytes, whereby alterations in a product can be detected, including (1) dilution of an analyte, (2) substitution of an ingredient for an analyte, (3) addition of a compound which alters interaction of the light emissive compound with an analyte and (4) addition of a compound which quenches light emission resulting from interaction of a light emissive compound with an analyte. Most frequently the alteration detected is in the amount of analyte bound to the light emissive compound, which is reflected by the intensity of light emitted when a sample is irradiated.

By "interacts with", as used herein, it is meant reacting, intercalating, binding or any other interaction which causes the dye to alter its light emission properties when irradiated.

The term "key ingredient," as used herein, means a component included in a composition of a product that is important in identifying the particular product.

The term "trace compound," as used herein, means a compound that is present in low concentrations (egg., at ppm or ppb levels) in a product. The trace compound can be related, for example, to a particular key ingredient. The trace compound can be introduced at the source of the key ingredient or during the manufacture of the product.

The invention can include one or more of the following advantages. The method can be used in the distilled spirits industry, where trace compounds and key ingredients can be measured using specific light-emissive compounds. Further, light-emissive compounds that indicate the source of ethanol can be used to determine the authenticity of a product. For example, spirits derived from yellow dent corn contain different trace compounds than spirits derived from cane sugar.

Moreover, although colas, and other soft drinks, contain similar levels of key ingredients, the levels key ingredients can be used to determine whether a particular manufacturer is diluting the concentrate to the appropriate level. For example, caffeine can be a targeted ingredient for light-emissive compounds in the analysis of soft drinks. Additional targets in soft drinks can include, but are not limited to, the high fructose corn syrup and the pH.

Furthermore, perfumes, fragrances, flavors, foods, and all types of beverages can be fingerprinted, using the methods of the invention, without adding any reagents to the product the user is going to consume. An advantage of invention is that exogenous product tags need not be added. Instead, native analytes of the product can be assayed. This is particularly important in determining authenticity of food products, where it is undesirable to add tags which could affect taste, odor, consistency and the like and might even be harmful to health when ingested. This is of great importance to many companies which are reluctant to adulterate their products.

The invention also is useful in identifying pharmaceutical active ingredients and/or excipients. The invention, therefore, can be used to authenticate pharmaceutical or other chemical products. In the instance where a fingerprint is obtained for a pharmaceutical formulation, an identical fingerprint may permit an inference that the pharmaceutical formulation was prepared by a particular process, which itself may be a patented process. In addition, there may be unique ingredients used in a patented process, the presence and concentration of which can be used to determine the authenticity of a material manufactured by that process (when the material contains trace levels of the unique ingredients) or as evidence of infringement of the patented process. Thus, single or multiple dyes can be selected or developed to identify compounds or excipients that would be present (or present at particular concentrations) only as a result of performing a patented process.

The invention allows accurate light-emissive profiles of products to be determined and monitored without altering the product.

Another advantage of the invention is that it is unnecessary to know or determine the composition of the product in order to select light emissive compounds and to develop assays for determining accurately authenticity. Thus, it is unnecessary to know or determine the formula for Coca-Cola® or Pepsi® in order to test the authenticity of products sold under those trademarks. This is to be contrasted with many infrared methods (e.g., near IR, mid IR and Fourier Transform IR), that often result in gathering sufficient information to determine the composition of a product being tested. This advantage of the present invention is of great importance to companies reluctant to identify the secret ingredients of their products.

A further advantage of the invention is that the use of light-emitting compounds results in a sensitivity level that far exceeds the sensitivity levels achievable by the use of Fourier Transform IR methods.

Other features and advantages of the invention will be apparent from the following detailed description thereof, and from the claims.

DETAILED DESCRIPTION OF THE INVENTION

Figure 1:
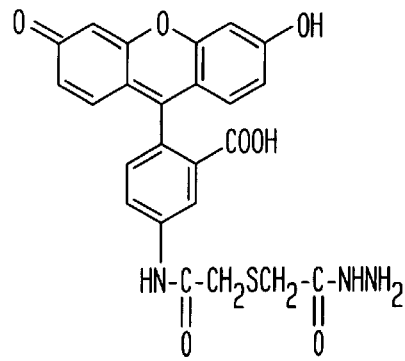
FIG. 1 is a drawing that shows the chemical structures of Compounds 1–13.
Figure 1:
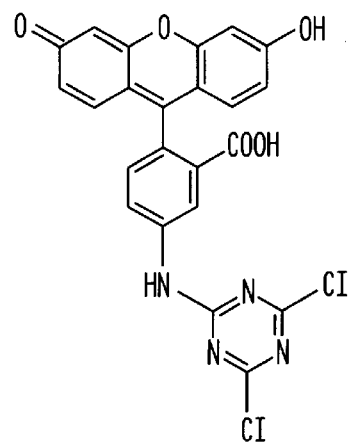
Figure 1:
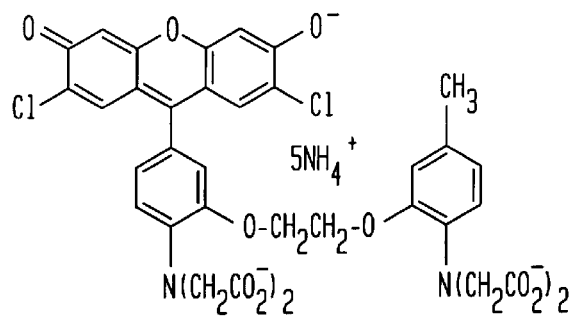
Figure 1:
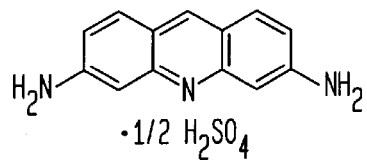
Figure 1:
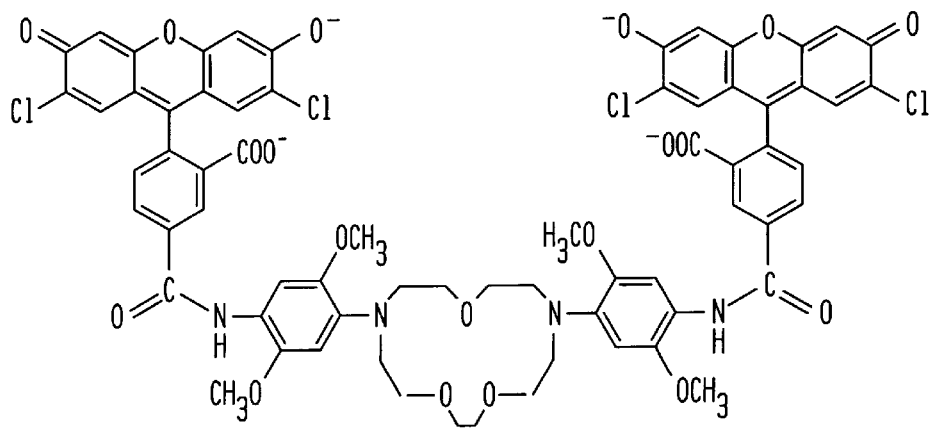
Figure 1:
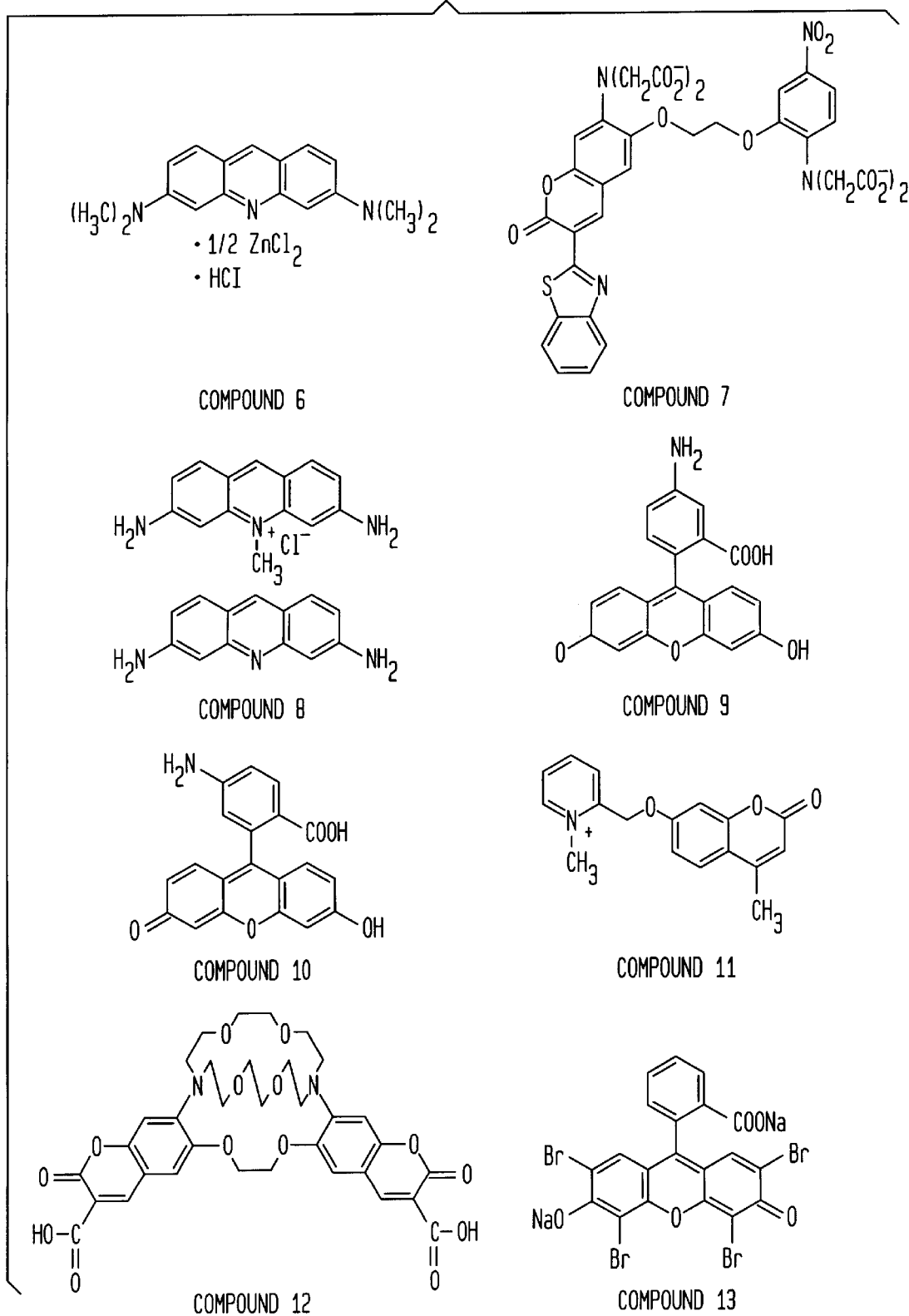

The invention features an automated method for analyzing analytes such as key ingredients and the relative amounts of analytes such as key ingredients in products which in turn enables authentication and monitoring products for fraud and quality control. Particular light-emissive compounds can be used to identify and quantitate the relative levels of analytes such as key ingredients in the products.

One method for identifying counterfeit or altered products relies on the development of a group of between two and seven specific light-emissive compounds for a single product along with specialized automated handling methods and new data analysis. These methods can be used to provide a method which is simpler to use than prior techniques and which can be performed rapidly using conventional and generally available equipment. It is a further aspect of the invention to provide a technique which gives quantitative measure of the degree to which the product is altered or tampered with. It is a further aspect of the invention to provide methods and compounds for identifying key-product ingredients.

The invention provides a method for determining the relative amounts of analytes in a product by exposing the products to selected light-emissive compounds present in a light-emissive compound. Analytes are selected so that in the presence of the analyte, the compounds can interact with (e.g. partition, intercalate, or bind to) the analytes in the aqueous and/or organic liquid fractions of the product. The interaction between the components of the product and the light-emissive compound induces a chemical change that can be detected using automated light emissive detection systems. Light-emission can include luminescence, fluorescence, or phosphorescence. Fluorescence is described, for example, in "Practical Fluorescence," Second Edition, G. G. Guilbault, Editor, Marcel Dekker, Inc., 1990, which is incorporated herein by reference.

In general, a sample of the product and the light emissive compound are mixed. The light-emissive compounds and analytes in the product are allowed to react for a period of time and temperature that is specific for each product and light-emissive compound, for example, until light emission from the mixture no longer changes with time. Bandpass and cutoff filters are used to isolate excitation wavelengths from emission spectra due to light emission from the sample. Change in light emission due to the interaction can be determined, from the formula [(Fd−Fp)/Fd]×lOO, where the light emission of the light emissive compound in the absence of product is Fp, and the light emission after exposing the light-emissive compound to the product is Fd. The light emission changes as a result of interactions of the light-emissive compound with analytes in the product. Light emission also can change due to indirect influences, such as quenching by an ingredient of an adulterated product.

The light-emissive compound can include two light-emissive compounds and can be added together in the same sample well, if the emission maximum of the dyes is more than 40 nm apart. The wavelength filter must be changed for each light-emissive compound being observed. There is no practical limit to the number of light-emissive compounds that can be used to demonstrate the specific presence of a particular analyte. The number of light-emissive compounds can be increased to indicate the specific presence of an ingredient or to rule out possible non-specific analysis of closely related compounds.

It is possible to determine the authenticity of product if the trace or chemical structure of the analyte or product is unknown, preferably by using between three and seven individual light-emissive compounds in the light-emissive compound. Using an automated robotics workstation (e.g., the Beckman Biomek 1000), it is possible to combine the light-emissive compounds in random order with the product standards in a microwell plate. Once a detectable light emission pattern is developed for all the standards, a single test product can be added to the same microwell plate (e.g., up to 99 standards and 1 single test product). The light emission output of the sample is compared to each of the standards on the plate run. In this way, it is possible to determine authenticity without developing a prior record of standard light emission levels.

There are many examples of light-emissive compounds that can be included in the light-emissive compound, some of which are shown in FIG. 1 (Compounds 1–13). Compound 1 is 5-(2-carbohydrazinomethylthioacetyl) aminofluorescein. Compound 2 is 5-(4,6-dichlorotriazinyl) aminofluorescein. Compound 3 is Fluo-3 pentaammonium salt. Compound 4 is proflavine hemisulfate (3,6-dimethylaminoacridine hemisulfate). Compound 5 is tetra (tetramethylammonium) salt. Compound 6 is acridine orange hydrochloride hydrate. Compound 7 is BTC-SN. Compound 8 is acriflavine. Compound 9 is 4-aminofluorescein. Compound 10 is 5-aminofluorescein. Compound 11 is sulfite blue coumarin. Compound 12 is courmarin diacid cryptand (CD222). Compound 13 is Eosin Y.

Infrared light emissive compounds, including those emitting in the near infrared wavelengths, can improve performance in certain circumstances because of the low endogenous background fluorescence of many materials in the infrared region. The addition of infrared dyes allows for a significant increase in certain circumstances in signal to noise ratio in an aqueous environment. Examples include porphyrins, cyanines, naphthoquinone methides, squarylium dyes, polymethines, etc. Most common are the cyanines including metal-containing phthalocyanines, pentamethines, naphthalocyanines, merocyanines, tricarboncyanines, indocyanines and isothiocyanato-functionalized cyanines.

Some examples of the liquid products that can be analyzed and the light-emissive compounds that can provide distinctive and significant analyses of the products are: alcohol-based products such as neutral spirits, vodka, and tequila that can be analyzed, for example, with Compounds 1, 2, 3, 4, 5, 6, 7, 8, or 9; sucrose and high fructose based products such as soft drinks (e.g., Coca-Cola and Pepsi) that can be analyzed, for example, with Compounds 1, 2, 3, or 9; and infant formulas such as Similac, Carnation, Enfamil that can be analyzed, for example, with Compounds 1, 2, 3, or 7. It should be understood that a liquid sample may be obtained from a liquid product or from nonliquid products (e.g., by dissolving a solid or semisolid, by extraction of a solid and dissolution of the extracted material or the like).

The methods of the invention can be used to analyze other liquid products as well as liquid samples derived from other products, based on the correct choice of light emissive compounds used in the analysis. For example, light-emissive compounds that are amine-containing (e.g., Compound 1) and light-emissive compounds that are reagents for modifying amines, alcohols, arginine, guanosine,' and polysaccharides (e.g., Compound 2) can be used in product authenticity/monitoring and testing of, for example, neutral spirits, distilled spirits, infant formula, or soft drinks. In addition, light-emissive chemicals that are calcium indicators (e.g., Compound 3) or are capable of complexing with $Cd^{2+}$, $Zn^{2+}$, $Pb^{2+}$ and $Ba^{2+}$ (e.g., Compound 7) can be used for product authenticity/monitoring testing of neutral spirits, distilled spirits, or soft drinks. Light-emissive acridine compounds (e.g., Compound 6) are capable of complexing with lipids and fats for product authentication or monitoring of distilled spirits or infant formulas. Light-emissive acriflavine compounds that interact with alcohols (e.g., Compound 8) are useful for product authentication/monitoring testing of neutral and distilled spirits. Light-emissive chemicals that react with primary alcohols, aldehydes or ketones (e.g., Compounds 9 and 10) are useful for authentication or monitoring of neutral spirits, distilled spirits, or soft drinks.

Selection of Light-Emissive Compounds

Light-emissive compounds can be selected, based on one or more of the following properties: (1) a light-emissive compound in the composition should interact with an analyte in the product; (2) a light-emissive compound in the composition should interact with an analyte in the product in a concentration dependent manner; (3) a light emissive compound and the interaction product(s) should be stable and the interaction should be repeatable; (4) similar lot numbers of the product should interact the same way with the light-emissive compound; and (5) the light-emissive compound should interact differently with closely related products on the basis of the chemical structures of key ingredients in the product (e.g., to discriminate between brand names of a product, such as between, for example, Smirnoff and Absolut vodkas). In many situations, it is desired that multiple light emissive compounds be identified to authenticate or monitor a single consumer product.

To determine a light-emissive compound that can be used in the analysis of a product, the chemical structure of analytes in the selected product need not be known, but can be chosen, or assumed to be present in the product. At least one analyte is targeted in a particular product. A candidate light-emissive compound can generally be selected using the guidelines, described above, along with the information listed in Table 1 and Table 2. The information listed in the tables is not intended to be limiting, but provides general information that can be useful in the selection of a light-emissive compound. Table 1 lists reactive groups in light-emissive compounds that can be useful for identifying particular functional groups in a key ingredient of the product. Table 2 lists selected useful initial light emissive compounds. The light emission from a sample containing a light-emissive compound (selected according to the guidelines as a result of interactions with analytes in the product) can be used to authenticate and monitor products for fraud and quality control.

One preferred method of selection is as follows. A product is selected. The product is diluted until its absorbance is below 0.02. A plurality of light emissive compounds such as dyes are selected. The dyes are diluted relative to one another so that they all will have an emission strength of between 200 and 2000 fluorescence units per ml when 1.4 $\mu$l of dye is added to 1 ml of diluted product (typically between 0.3 and 500 micromolar). A series of dilutions of product then are prepared (all being below 0.02 absorbance). This, for example, might be dilutions of product such as 1:10, 1:15, 1:20, 1:25 and 1:30. Dyes are added to these dilutions at 1.4 $\mu$l dye/ml diluted product. Dyes also are added similarly to (1) an acceptable, but altered, standard (such as a standard diluted only 5%) and (2) an unacceptable, but altered, standard (such as a standard diluted by >10%) and (3) a nonauthentic but closely related product (such as Pepsi® where the product is Coca-Cola®). Tests are run in quadruplicate. A fingerprint is generated electronically for the standard, and an acceptable range which includes the acceptable altered product but excludes the nonacceptable and nonauthentic products is determined electronically, using software and mathematical formulas such as is described below, pre-selecting the confidence limits (e.g. two standard deviations, three standard deviations, etc.). Multiple dyes are run simultaneously in 96 well plates which are read automatically. Dyes then are selected based upon their ability to distinguish authentic and acceptable products from nonauthentic and nonacceptable products. Further calibration can be carried out. First, a test dilution can be selected as that dilution which is 50% of the lowest dilution of product at which maximum fluorescence for a dye is achieved. Then variables such as temperature, time of incubation and unacceptable or nonauthentic products can be varied, preferably measured in quadruplicate, to permit selection of dyes useful for a given product. As should be understood, using such screening methodology, panels of dyes for producing fingerprint profiles can be selected, without knowledge of the composition of the product or the analytes in the product to which the dye binds.

TABLE 1

| light-emissive compound reactive group | key ingredient functional groups |
|---|---|
| activated ester | amines or anilines |
| acyl azide | amines or anilines |
| acyl halide | amines, anilines, alcohols or phenols |

TABLE 1-continued

| light-emissive compound reactive group | key ingredient functional groups |
|---|---|
| acyl nitrile | alcohols or phenols |
| aldehyde | amines or anilines |
| alkyl halide | amines, anilines, alcohols, phenols or thiols |
| alkyl sulfonate | thiols, alcohols or phenols |
| anhydride | alcohols, phenols, amines or anilines |
| aryl halide | thiols |
| aziridine | thiols or thioethers |
| carboxylic acid | amines, anilines, alcohols or alkyl halides |
| diazoalkane | carboxylic acids |
| epoxide | thiols |
| haloacetamide | thiols |
| halotriazine | amines, anilines or phenols |
| hydrazine | aldehydes or ketones |
| hydroxyamine | aldehydes or ketones |
| imido ester | amines or anilines |
| isocyanate | amines or anilines |
| isothiocyanate | amines or anilines |

TABLE 2

| light-emissive compound | analyte |
|---|---|
| acridine orange | |
| acid alizarin Garnet R | alcohol |
| 9-amino acridine | ethanol |
| anthracene | ethanol |
| chlorophyll A | ethanol/methanol |
| chlorophyll B | methanol |
| eosin | |
| FAD | |
| indole | |
| naphthalene | alcohol |
| NADPH | |
| prolamine | |
| protoporphyrin I | |
| pryodoxal | |
| pyridoamine-5-phosphate | |
| quinacrine | |
| quinine | |
| 6-methoxyquinoline | |
| phenanthrene | alcohol |
| resorcinol | |
| rhodamine 3G (or 6G) | |
| riboflavin | |
| salicylic acid | |
| serotonin | |
| skatole | |
| sulfanilic acid | |
| sodium salicylate | water |

Another light-emission tool for product identification is the standard light emission phenomenon called impurity quenching. Even in dilute solutions, impurities can cause measurable quenching of light emission. The specific amount of quenching can be exploited to identify a specific lot or batch of a product. See, for example, "Practical Fluorescence," G. G. Guilbault, Editor, page 32. It is also possible that the light emission wavelength of the light-emissive compound can shift in the presence (or absence) of an ingredient in the product. This shift can be used to quantify the amount of ingredient present in the product.

Regional production differences can be determined using two different methods. One method involves identifying compounds of regional specificity from differences in starting materials. Different suppliers of ingredients in a product will leave different levels of trace compounds in their supplied materials. Even though these trace compounds are present at extremely low levels, the light-emissive compounds are sensitive to a level of parts per million and even to parts per billion in some cases. For example, the trace levels of compounds, such as aldehydes and methanol, can be used to identify different varieties (i.e., suppliers) of sucrose and high fructose corn syrup in fruit and cola consumer products. In another example, ethanol distilled from corn contains different trace components than ethanol distilled from cane sugar. The identification and analysis of these trace elements can be used to detect product authenticity or detect backfilling (dilution) of a particular product.

A second method of determining regional differences in a product involves analysis of trace elements (or compounds) in, for example, the water used to dilute the consumer product. The trace elements (or compounds) can be used as a specific lot number marker. Specifically, levels of calcium, magnesium and/or heavy metals can be used to identify products by "specific lot number water identity."

Additionally, a company's processes can result in a detectable amount of at least one other trace material that can identify the companies specific product. The identity and quantity of the trace materials make it possible to identify the lot number of a specific production run. For example, many colas have a fixed level of caffeine in the concentrate and in the final product. Light-emissive compounds that indicate caffeine concentrations can be developed according to methods described herein.

The relative amounts of key ingredients in a sample can be determined by light emission analysis. The light emission measurement can be used in combination with other trace light emission analysis to determine authenticity. For example, vodka must contain 50% ethanol to legally be called vodka. Additionally, this method can be used to identify a lot number or batch number or to determine the authenticity of, for example, orange juice, apple juice, or lemon juice.

The relative amounts of water can be compared in a standard sample standard and a suspect sample using, for example, the naphthylamine light-emissive dyes. Sulfonated naphthylamines, such as 2-p-toludinylnaphthalene-6-sulfonate (2,6-TNS) and 1-anilino-8-naphthalenesulfonate (1,8-ANS), shift light emission wavelength in water. The relative amount of shift depends on the amount of water in a sample. For example, in water, the spectral sensitivity is substantially shifted to longer wavelengths, and the light emission quantum yield and decay times decrease.

Data Analysis

Multi-variant analysis can be used to analyze the light emission results of each product sample with each light emissive compound. Typically, the results are interpreted in comparison to light emission from a standard product sample treated in the same way, or a "fingerprint." All samples can be analyzed for the presence of key ingredient using a light-emissive compound containing a single light-emissive compound or a combination of light-emissive compounds. The largest and smallest mean values are determined for each set of product samples using four independent measurements made of the same sample (n=4). The multiple comparison procedure allows the determination of a critical value (e.g., at a 95% confidence level) for the difference between the largest and the smallest sample means, which relates to the differences in the respective products. A difference in the sample means, that is equal to or greater than the critical value, suggests a significant difference in the products. A significant difference can imply different product treatments, starting materials and compositions.

Typically, the analysis involves Tukey Multiple Comparison Procedure conducted, e.g., at a 95% confidence level ($\alpha 0.05$). The Multiple Comparison Procedure assumes that the number of sample means, k, are based on independent random samples, each containing the same number of observations, n. In this case, s, the standard deviation is the square root of the mean square errors (MSE) of the sample means. The MSE has a number of degrees of freedom, v, associated with it. From k,v, and $\alpha$, the critical value of the Studentized range, $q_\alpha(k,v)$, can be determined (see, for example, Biometrika Tables, Vol. 1, E. L. Pearson and H. O. Harily, eds., Cambride University Press, Cambridge (1966)). It then follows that the distance, omega (T) is $$\omega = q_\alpha(k, v) \frac{s}{N^{0.5}}$$

Tukey analysis can allow the identification of sample means that do not match the standard products. If two measurements differ by a value greater than omega, then the two samples are different. If not, the samples are pairs have substantially similar compositions (i.e., are the same composition, but could be different batches). Each light-emissive compound/product sample system can be considered a single variant. Combining the analyses for each of the light-emissive compounds together can lead to a multi-variant analysis program that we have developed a software program for. That this multi-variant light-emissive product authenticity analysis can be carried out using, for example, spread-sheet type computer programs.

While Tukey analysis has been described herein, it is to be appreciated that other multi-variant methods of analysis may be used. Such alternate methods include, for example, Duncan's multiple range analysis and Newman-Kuls analysis, as described in Biostatistical Analysis, 3rd Edition, J. H. Zar, Prentice-Hall, Upper Saddle River, N.J. (1996).

Figure 2:
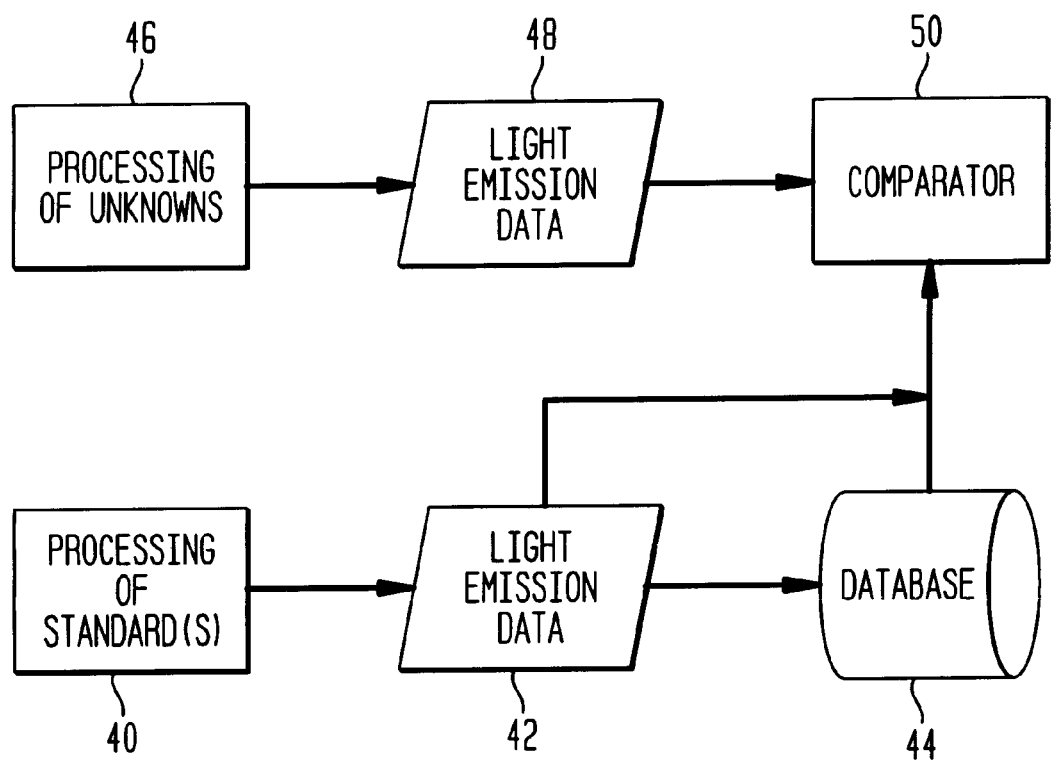
FIG. 2 is a data flow diagram.

FIG. 2 is a data flow diagram representing the overall processing in this system of the invention. Standard samples are processed with selected compounds by first processing system 40 to produce light emission results 42. It is possible that these light emission results could be stored in a database 44. Similarly, unknown samples are processed by a processing system 46 using the same selected compounds. The processing system 46 produces light emission results 48, i.e., a fingerprint for each unknown sample. A comparison procedure is performed by a comparator 50 to produce an indication of the authenticity of the sample. The comparison can be performed using the Tukey multiple comparison procedure described above. This computer may receive the data from the light emission results from processing systems 40 and 46 either directly from those systems or over a computer network. The comparator also may receive the fingerprint of the standard samples from a database which may be either local to or remote from the computer running the comparison procedure.

A suitable computer system to implement the comparator 50 typically includes a main unit connected to an output device, such as a display, and an input device, such as a keyboard. The main unit generally includes a processor connected to a memory system via an interconnection mechanism. The input device is also connected to the processor and memory system via the connection mechanism, as is the output device.

It should be understood that one or more output devices may be connected to the computer system. Example output devices include a cathode ray tube (CRT) display, liquid crystal displays (LCD), printers, communication devices such as a modem, and audio output. It should also be understood that one or more input devices may be connected to the computer system. Example input devices include a keyboard, keypad, track ball, mouse, pen and tablet, communication device, audio input and scanner. It should be understood the invention is not limited to the particular input or output devices used in combination with the computer system or to those described herein.

The computer system may be a general purpose computer system which is programmable using a high level computer programming language, such as "C", or "Pascal". The computer system may also be specially programmed, special purpose hardware. In a general purpose computer system, the processor is typically a commercially available processor, of which the series x86 processors, available from Intel, and the 680X0 series microprocessors available from Motorola are examples. Many other processors are available. Such a microprocessor executes a program called an operating system, of which UNIX, DOS and VMS are examples, which controls the execution of other computer programs and provides scheduling, debugging, input/output control, accounting, compilation, storage assignment, data management and memory management, and communication control and related services. The processor and operating system define a computer platform for which application programs in high-level programming languages are written.

A memory system typically includes a computer readable and writeable nonvolatile recording medium, of which a magnetic disk, a flash memory and tape are examples. The disk may be removable, known as a floppy disk or an optical disk, or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and then copies the data to the disk when processing is completed. A variety of mechanisms are known for managing data movement between the disk and the integrated circuit memory element, and the invention is not limited thereto. It should also be understood that the invention is not limited to a particular memory system.

It should be understood the invention is not limited to a particular computer platform, particular processor, or particular high-level programming language. Additionally, the computer system may be a multiprocessor computer system or may include multiple computers connected over a computer network.

Materials and Methods

The methods were developed to optimize analysis or determine the authenticity or tampering of a product in the water and/or organic component of the product. The general methods for using Compounds 1–10 are generally described below.

A Beckman Biomek 1000 automated workstation (Beckman Instruments, Columbia, Md.) was used to make dilutions and place 150 microliters of the light-emissive compound into a test plate, although any automated dispensing workstation can be used. The test plate can be made from any suitable material and can have any number of wells, such as 6, 24, 96 or 384 wells (Corning-Costar, Falcon-Collaborative, microwell test plates). The light emission of the light emissive compound in the absence of product is Fp, and the light emission after exposing the light-emissive compound to the product is Fd. The Fd and Fp light emission analysis for the purpose of these experiments was made using a Molecular Dynamics FluorImager 575, but any microplate reader can be used (e.g., Cytofluor). Bandpass and cutoff filters are used to isolate excitation wavelengths from emission spectra due to light emission from the sample. Fd light emission analysis was made for each chemical in each well of the test plate. Repetition of measurements allows correction for systematic variability due, for example, to automatic pipetting (<5%). Next, 150 microliters of product are added to the chemicals in the microwells using the Beckman Biomek 1000 automated workstation. The chemical and the product are allowed to react for a period of time and temperature that is specific for each product and chemical. Change in chemical light emission due to the presence of the product is determined by calculation using the equation $[(Fd-Fp)/Fd] \times 100$.

In certain embodiments, an immutable standard, such as a ruby or other precious stone, may be used to compensate for variations in the laser output signal intensity. For such embodiments, the immutable standard can be placed in one of the wells of the test plate.

Compound 1, 5-(2-carbohydrzinomethylthioacetyl) aminofluorescein, was obtained from Molecular Probes, Inc., Eugene, Oreg., Lot 2841-1. The final concentration of the working solution can range between 0.5 and 10 micromolar. Compound 1 has an excitation maximum at 488 nm at neutral pH and 356 nm at pH 8. Compound 1 has an emission maximum at 520 nm. See, R. E. Hileman, et al., Bioconjugate Chem. 5:436 (1994) for the synthesis of the compound.

Compound 2 and Compound 3 should be used in the method together. Compound 2, 5-(4,6-dichlorotriazinyl) aminofluorescein, was obtained from Molecular Probes, Inc., Eugene, Oreg., Lot 2851-1. A stock solution of Compound 2 was prepared in dimethyl sulfoxide (DMSO, ACS reagent, Sigma Chemical, St Louis, Mo.). The final concentration of the working solution can range between 0.5 and 10 micromolar. Compound 2 has an excitation maximum at 495.7 nm and emission maximum at 516.3 nm. For a reference that describes the original use of this compound, see, Barskii et al., Izv. Akad. Nuak SSSR, V. E. (1968) PN 101.

Compound 3, Fluo-3, pentaammonium salt, was obtained from Molecular Probes, Inc., Eugene, Oreg., Lot 2641-6. The final concentration of the working solution can range between 0.5 and 10 micromolar. Compound 3 has an excitation maximum at 510 nm and emission maximum at 530 nm. Fluo-3 was developed for measuring calcium levels in cellular experiments. See, for example, Tsien, R., et al., J. Biol. Chem. 264:8171 (1989).

Compound 4, proflavine hemisulfate (3,6-diaminoacridine hemisulfate) was obtained from Sigma-Aldrich, St. Louis, Mo. The final concentration of the working solution can range between 0.5 and 10 micromolar. Compound 4 has an emission maximum at 515 nm in methanol. Proflavine was developed as a fabric dye and for cell staining procedures. See, for example, Chan, L. M., et al., Biochem. Biophys. Acta, 204:252 (1970).

Compound 5, tetra(tetramethylammonium) salt, was obtained from Molecular Probes, Inc., Eugene Oreg. The final concentration of the working solution can range between 0.5 and 20 micromolar, depending on the product tested. Compound 5 has an excitation maximum at 488 nm and an emission maximum around 535 nm. Compound 5 was developed at Molecular Probes as Sodium Greenlm for the fluorometric determination of Na+ concentrations.

Compound 6, acridine orange hydrochloride hydrate, obtained from Sigma-Aldrich, St. Louis, Mo. The final concentration of the working solution can range between 0.5 and 20 micromolar. Compound 6 has an excitation maximum at approximately 490 nm and emission maximum at 519 nm. Compound 6 can be used for printing inks and as a stain for fats and lipids in biological samples. See, for example, Clark, G., "Staining Procedures" ed. Williams and Wilkins, Baltimore 1981 pp. 48, 57, 61, 71, 72, 86, 87, 89, 90, and 429.

Compound 7, BTC-5N (Costlei et al., J. of Chem. Society Perkins translation 2, p. 1615), was obtained from Molecular Probes, Inc., Eugene, Oreg. The final concentration of the working solution can range between 0.5 and 20 micromolar. Compound 7 has an excitation maximum at approximately 415 nm and an emission maximum at 515 nm.

Compound 8, acriflavine, is composed of an approximate 8 to 1 mixture of 3,6-diamino-10-methylacridinium chloride and 3,6-diaminoacridine, and was obtained from Sigma-Aldrich, St.-Louis, Mo. The working solution concentration can range between 0.5 and 20 micromolar, depending on the product tested. Compound 8, in its neutral form, has an excitation maximum in ethanol at 483 nm and an emission maximum at 517 nm with a long-lasting emission state that can be used to identify the relative levels of ethanol in a sample. The long-lasting emission in ethanol is noted by Furumoto, H. W. and Ceccon, H. L., IEEE J. Quantum Electron., QE-6, 262, (1970). Compound 8 is an ordinary biological stain and is useful as a light-emissive compound and a Schiff reagent. See, for example, "Conn's, Biological Stains," 9th ed.: Lillie, R. D., Ed.; Williams and 25 Wilkins: Baltimore, 1977; p. 355.

Compound 9, 4-aminofluorescein, was obtained from Sigma-Aldrich, St. Louis, Mo. The working solution concentration can range between 0.5 and 20 micromolar, depending on the product tested. Compound 9 has an excitation maximum at 496 nm and an emission maximum at 530 nm. See, for example, Coons, A. H., et al., J. Exp. Med. 91:1–14 (1950).

Compound 10, 5-aminofluorescein, obtained from Sigma-Aldrich, St. Louis, Mo., was used in a similar manner and at similar concentrations as Compound 9. The emission is at 530 nm. Glabe et al, Anal. Biochem, 130:287–294 (1983).

Compound 11, sulfite blue coumarin, S-6902, was obtained from Molecular Probes, Eugene, Oreg. Compound 11 has an excitation maximum at 325 nm and an emission maximum at 373 nm. Compound 11 can be useful for measuring sulfites. Sulfite contamination in high fructose corn syrup is a problem well known in the corn processing and milling industry.

Compound 12, courmarin diacid cryptand (CD222) (Costlei et al., J. of Chem. Society Perkins translation 2, p.1615), was obtained from Molecular Probes, Eugene, Oreg. Compound 12 is a ratio dye with an excitation maximum at 365 nm and emission maximum at 465 nm. Compound 12 is a potassium sensitive dye, enabling authentication based potassium benzoate, a preservative in many cola drinks.

Compound 13, Eosin Y, was obtained from SigmaAldrich, certified Grade, St. Louis, Mo. Compound 13 has an excitation maximum at 522 nm and an emission maximum at 551 nm. Compound 13 is a ph-sensitive light-emissive compound.

EXAMPLE 1

Neutral Spirits

The analysis methods of the invention can be used in the wine and distilled spirits industry to determine product authenticity, defend international trademarks, document product quality, and detect product backfilling (i.e., dilution with lower quality ingredients). In this industry, the origin and source of the ethanol in a product can be used to determine product authenticity. The product label must correctly represent the contents in a manufacturer's bottle. Previously, there was no practical method for determining the source of ethanol or neutral spirits (96% ethanol).

A double blind experiment was conducted to determine the differences between 6 neutral spirits samples. In addition, if there were duplicates, the experiment was designed to identify the duplicates.

The neutral spirits product origins can be identified from the data presented in Table 3 and Table 4. Referring to Table 3, the level of light emission upon excitation was monitored in an array of six samples (10-1, 10-2, 10-3, 10-4, 10-5, and 10-6) that were each tested four times (A, B, C, and D) with a pair of light-emissive compounds. Within each set, each sample of the product was tested four times with a light-emissive compound. The excitation wavelength was 522 nm. The light-emissive compounds were Compound 2 and Compound 3.

Stock solutions of the light-emissive compounds were prepared by dissolving Compound 2 in DMSO at a concentration of 2 mM and Compound 3 in DMSO at a concentration of 1 mM.

The concentrations of the working solutions of light-emissive compounds were optimized against known samples of neutral spirits. The optimum concentrations were determined from the concentrations of light-emissive compounds that provides emission intensities that are capable of discriminating known neutral spirits samples from other samples by a value greater than omega. The working solution of Compound 2 was prepared by diluting 120 uL of the stock solution dye in 20 mL of distilled water. The working solution of Compound 3 was prepared by diluting 100 $\mu$L of the stock solution in 20 mL of distilled water.

Both Compound 2 and Compound 3 require a 530BP+15 nm band pass filter to reduce the excitation wavelength intensity during the emission measurements. The intensity of the emission was measured in relative fluorescence units

TABLE 3

| | STATISTICAL DATA | | | | NEUTRAL SPIRITS | | | |
|---|---|---|---|---|---|---|---|---|
| | A 10-1 | A 10-2 | A 10-3 | A 10-4 | A 10-5 | A 10-6 | B 10-1 | B 10-2 |
| Measurement 1 | 0.2276 | −0.5481 | −0.2021 | −0.2030 | −0.5479 | 0.1773 | 0.2088 | −0.5474 |
| Measurement 2 | 0.2299 | −0.5454 | −0.1991 | −0.1979 | −0.5354 | 0.2096 | 0.2363 | −0.5417 |
| Measurement 3 | 0.2384 | −0.5471 | −0.2095 | −0.1966 | −0.5479 | 0.1811 | 0.2148 | −0.5524 |
| Measurement 4 | 0.2468 | −0.5573 | −0.1982 | −0.1939 | −0.5434 | 0.1932 | 0.2113 | −0.5548 |
| Variance: | 7.618E-05 | 2.866E-05 | 2.629E-05 | 1.467E-05 | 3.466E-05 | 2.119E-03 | 1.584E-04 | 3.377E-05 |
| Mean: | 0.2357 | −0.5495 | −0.2022 | −0.1978 | −0.5437 | 0.1903 | 0.2178 | −0.5491 |
| | B 10-3 | B 10-4 | B 10-5 | B 10-6 | C 10-1 | C 10-2 | C 10-3 | C 10-4 |
| Measurement 1 | −0.2395 | −0.2079 | −0.5699 | 0.1670 | 0.2480 | −0.5471 | −0.1908 | −0.1828 |
| Measurement 2 | −0.2116 | −0.2309 | −0.5627 | 0.2337 | 0.2683 | −0.5383 | −0.1899 | −0.1886 |
| Measurement 3 | −0.2424 | −0.2381 | −0.5637 | 0.1677 | 0.2759 | −0.5330 | −0.1883 | −0.1862 |
| Measurement 4 | −0.2312 | −0.2292 | −0.5769 | 0.1810 | 0.2501 | −0.5356 | −0.1911 | −0.1756 |
| Variance: | 1.936E-04 | 1.689E-04 | 4.32E-05 | 9.967E-04 | 1.876E-04 | 3.765E-05 | 1.506E-06 | 3.184E-05 |
| Mean: | −0.2312 | −0.2265 | −0.5683 | 0.1874 | 0.2606 | −0.5385 | −0.1900 | −0.1833 |
| | C 10-5 | C 10-6 | D 10-1 | D 10-2 | D 10-2 | D 10-4 | D 10-5 | D 10-6 |
| Measurement 1 | −0.5449 | 0.2154 | 0.2435 | −0.5597 | −0.2321 | −0.2200 | −0.5633 | 0.1974 |
| Measurement 2 | −0.5615 | 0.2234 | 0.2609 | −0.5486 | −0.2191 | −0.2104 | −0.5626 | 0.2431 |
| Measurement 3 | −0.5488 | 0.2247 | 0.2687 | −0.5496 | −0.1994 | −0.1999 | −0.5552 | 0.2597 |
| Measurement 4 | −0.5453 | 0.2428 | 0.2861 | −0.5452 | −0.2055 | −0.1891 | −0.5466 | 0.2766 |
| Variance: | 6.4044E-05 | 1.341E-04 | 3.124E-04 | 3.882E-05 | 2.134E-04 | 1.776E-04 | 6.078E-05 | 1.161E-03 |
| Mean: | −0.5501 | 0.2266 | 0.2648 | −0.5508 | −0.2141 | −0.2048 | −0.5570 | 0.2442 |

MSE = 0.0001835
OMEGA = 0.0354918

TABLE 4

Fingerprint Data

| | A 10-1 | A 10-2 | A 10-3 | A 10-4 | A 10-5 | A 10-6 | B 10-1 | B 10-2 | B 10-3 | B 10-4 | B 10-5 | B 10-6 |
|---|---|---|---|---|---|---|---|---|---|---|---|---|
| A 10-1 | 0 | 1 | 1 | 1 | 1 | 1 | 0 | 1 | 1 | 1 | 1 | 1 |
| A 10-2 | 1 | 0 | 1 | 1 | 0 | 1 | 1 | 0 | 1 | 1 | 0 | 1 |
| A 10-3 | 1 | 1 | 0 | 0 | 1 | 1 | 1 | 1 | 0 | 0 | 1 | 1 |
| A 10-4 | 1 | 1 | 0 | 0 | 1 | 1 | 1 | 1 | 0 | 0 | 1 | 1 |
| A 10-5 | 1 | 0 | 1 | 1 | 0 | 1 | 1 | 0 | 1 | 1 | 0 | 1 |
| A 10-6 | 1 | 1 | 1 | 1 | 1 | 0 | 0 | 1 | 1 | 1 | 1 | 0 |
| B 10-1 | 0 | 1 | 1 | 1 | 1 | 0 | 0 | 1 | 1 | 1 | 1 | 0 |
| B 10-2 | 1 | 0 | 1 | 1 | 0 | 1 | 1 | 0 | 1 | 1 | 0 | 1 |
| B 10-3 | 1 | 1 | 0 | 0 | 1 | 1 | 1 | 1 | 0 | 0 | 1 | 1 |
| B 10-4 | 1 | 1 | 0 | 0 | 1 | 1 | 1 | 1 | 0 | 0 | 1 | 1 |
| B 10-5 | 1 | 0 | 1 | 1 | 0 | 1 | 1 | 0 | 1 | 1 | 0 | 1 |
| B 10-6 | 1 | 1 | 1 | 1 | 1 | 0 | 0 | 1 | 1 | 1 | 1 | 0 |
| C 10-1 | 0 | 1 | 1 | 1 | 1 | 1 | 1 | 1 | 1 | 1 | 1 | 1 |
| C 10-2 | 1 | 0 | 1 | 1 | 0 | 1 | 1 | 0 | 1 | 1 | 0 | 1 |
| C 10-3 | 1 | 1 | 0 | 0 | 1 | 1 | 1 | 1 | 1 | 1 | 1 | 1 |
| C 10-4 | 1 | 1 | 0 | 0 | 1 | 1 | 1 | 1 | 1 | 1 | 1 | 1 |
| C 10-5 | 1 | 0 | 1 | 1 | 0 | 1 | 1 | 0 | 1 | 1 | 0 | 1 |
| C 10-6 | 0 | 1 | 1 | 1 | 1 | 1 | 0 | 1 | 1 | 1 | 1 | 1 |
| D 10-1 | 0 | 1 | 1 | 1 | 1 | 1 | 1 | 1 | 1 | 1 | 1 | 1 |
| D 10-2 | 1 | 0 | 1 | 1 | 0 | 1 | 1 | 0 | 1 | 1 | 0 | 1 |
| D 10-3 | 1 | 1 | 0 | 0 | 1 | 1 | 1 | 1 | 0 | 0 | 1 | 1 |
| D 10-4 | 1 | 1 | 0 | 0 | 1 | 1 | 1 | 1 | 0 | 0 | 1 | 1 |
| D 10-5 | 1 | 0 | 1 | 1 | 0 | 1 | 1 | 0 | 1 | 1 | 0 | 1 |
| D 10-6 | 0 | 1 | 1 | 1 | 1 | 1 | 0 | 1 | 1 | 1 | 1 | 1 |

| | C 10-1 | C 10-2 | C 10-3 | C 10-4 | C 10-5 | C 10-6 | D 10-1 | D 10-2 | D 10-3 | D 10-4 | D 10-5 | D 10-6 |
|---|---|---|---|---|---|---|---|---|---|---|---|---|
| A 10-1 | 0 | 1 | 1 | 1 | 1 | 0 | 0 | 1 | 1 | 1 | 1 | 0 |
| A 10-2 | 1 | 0 | 1 | 1 | 0 | 1 | 1 | 0 | 1 | 1 | 0 | 1 |
| A 10-3 | 1 | 1 | 0 | 0 | 1 | 1 | 1 | 1 | 0 | 0 | 1 | 1 |
| A 10-4 | 1 | 1 | 0 | 0 | 1 | 1 | 1 | 1 | 0 | 0 | 1 | 1 |
| A 10-5 | 1 | 0 | 1 | 1 | 0 | 1 | 1 | 0 | 1 | 1 | 0 | 1 |
| A 10-6 | 1 | 1 | 1 | 1 | 1 | 1 | 1 | 1 | 1 | 1 | 1 | 1 |
| B 10-1 | 1 | 1 | 1 | 1 | 1 | 0 | 1 | 1 | 1 | 1 | 1 | 0 |
| B 10-2 | 1 | 0 | 1 | 1 | 0 | 1 | 1 | 0 | 1 | 1 | 0 | 1 |
| B 10-3 | 1 | 1 | 1 | 1 | 1 | 1 | 1 | 1 | 0 | 0 | 1 | 1 |
| B 10-4 | 1 | 1 | 1 | 1 | 1 | 1 | 1 | 1 | 0 | 0 | 1 | 1 |
| B 10-5 | 1 | 0 | 1 | 1 | 0 | 1 | 1 | 0 | 1 | 1 | 0 | 1 |
| B 10-6 | 1 | 1 | 1 | 1 | 1 | 1 | 1 | 1 | 1 | 1 | 1 | 1 |

TABLE 4-continued

| | | | | | | | | | | | | |
|---|---|---|---|---|---|---|---|---|---|---|---|---|
| C 10-1 | 0 | 1 | 1 | 1 | 1 | 0 | 0 | 1 | 1 | 1 | 1 | 0 |
| C 10-2 | 1 | 0 | 1 | 1 | 0 | 1 | 1 | 0 | 1 | 1 | 0 | 1 |
| C 10-3 | 1 | 1 | 0 | 0 | 1 | 1 | 1 | 1 | 0 | 0 | 1 | 1 |
| C 10-4 | 1 | 1 | 0 | 0 | 1 | 1 | 1 | 1 | 0 | 0 | 1 | 1 |
| C 10-5 | 1 | 0 | 1 | 1 | 0 | 1 | 1 | 0 | 1 | 1 | 0 | 1 |
| C 10-6 | 0 | 1 | 1 | 1 | 1 | 0 | 1 | 1 | 1 | 1 | 1 | 0 |
| D 10-1 | 0 | 1 | 1 | 1 | 1 | 0 | 1 | 1 | 1 | 1 | 1 | 0 |
| D 10-2 | 1 | 0 | 1 | 1 | 0 | 1 | 1 | 0 | 1 | 1 | 0 | 1 |
| D 10-3 | 1 | 1 | 0 | 0 | 1 | 1 | 1 | 0 | 1 | 0 | 1 | 1 |
| D 10-4 | 1 | 1 | 0 | 0 | 1 | 1 | 1 | 1 | 0 | 0 | 1 | 1 |
| D 10-5 | 1 | 0 | 1 | 1 | 0 | 1 | 1 | 0 | 1 | 1 | 0 | 1 |
| D 10-6 | 0 | 1 | 1 | 1 | 1 | 0 | 0 | 1 | 1 | 1 | 1 | 0 |

(rfu). The emission measurements are always made in the region of linear response, which on this fluorescence measuring instrument is made between 200 and 2000 rfu.

Each working solution (150 μL) was added to the test plate using an automated handling device with less than 5% error in volume measurement. The working solution/plate combination was measured for background fluorescence to account for variability in composition, plate dimensions, and laser output. Excitation and emission experiments can be run on any laser or non-laser fluorescence detection system. In this set of experiments the measurements were made using a FluorImager 575 (Molecular Dynamics, Sunnyvale, Calif.).

The neutral spirits samples were added directly to the sample plate. A key discovery in analyzing neutral spirits (96% ethanol) is that the analysis of the residual water is important. The signal from Compound 3 is designed to analyze the residual water. However, the high concentrations of ethanol in the samples masks the signal from the water. For this identification method to work well, the ethanol is removed under vacuum from the samples after they have been added to the individual microwells of the plate. This reduction allows the exact analysis of the water in the neutral spirits samples. Since the reduction takes place directly on the microwell plates, all samples are treated equally and the process is automated by placing a vacuum bell on the automated plate-handling work station.

The results of the experiment are presented in Table 3. Variance and mean were calculated for each group (A, B, C, or D) of 4 measurements. The 95% confidence levels were used for this fingerprint analysis. If two sample means differ by an amount greater than the omega, the samples are different (i.e., substantially different in composition). For example, in test A, sample 10-1 had a mean light emission intensity of 0.2357 and sample 10-2 had a mean light emission intensity of −0.5495. The difference in light emission intensity was 0.7852. The omega for test A was 0.0354918. If the difference (0.7852) is greater than omega (0.0354918) for any two samples, then the samples are different. Therefore, 10-1 and 10-2 are different. The comparison is made based strictly on the statistical data and can be done automatically, without the need for further interpretation.

The fingerprint data are presented in Table 4 to make all possible comparisons. A value of 1 in Table 4 indicates that the two sample means differ by more than omega. The value of 0 indicates that two samples do not differ by more than omega. Thus, a value of 0 signifies that the samples are pairs (i.e., substantially similar in composition, such as different batches or lots) or that the sample tested against itself (along the upper left-to-lower right diagonal of Table 4) and a value of 1 signifies that the samples are different. When sample pairs are consistently different, the samples are determined to have substantially different compositions (i.e., different brands altogether). As a result of the fingerprinting analysis in Table 4, products 10-1 and 10-6, 10-2 and 10-5, and 10-3 and 10-4 were determined to be pairs (i.e., substantially similar in composition) that are different from each other (i.e.,different lots).

EXAMPLE 2

Distilled Spirits

In a manner similar to that described in Example 1, it is possible to authenticate distilled spirits, such as vodka. For this fingerprint analysis, Compound 1, Compound 2, Compound 3, Compound 4, Compound 5, Compound 6, Compound 7, and Compound 8 can be used.

The stock solution of Compound 1 was 1.5 mM in a 1:1 DMSO/water mixture. The stock solution of Compound 2 was 2 mM in DMSO. The stock solution of Compound 3 was 0.5 mM in a 1:1 DMSO/water mixture. The stock solution of Compound 4 was 1 mM in DMSO. The stock solution of Compound 5 was 1 mM in distilled water. The stock solution of Compound 6 was 1 mM in DMSO. The stock solution of Compound 7 was 1 mM in distilled water. The stock solution of Compound 8 was 4 mg/mL in ethanol (chromatography grade, Sigma Chemical Company, St. Louis, Mo.).

Working solution concentrations were determined as in Example 1. The optimum concentration of light-emissive compound was determined to be the level that allows discrimination of known samples having value differences greater than omega. The working solution of Compound 2 was prepared by diluting 120 μL of the 2 mM stock solution in 20 mL of distilled water. The working solution of Compound 3 was prepared by diluting 100 μL of the stock solution in 20 mL of distilled water. The working solution of Compound 4 was prepared by diluting 100 μL of the stock solution in 50 mL of distilled water. The working solution of Compound 5 was prepared by diluting 75 μL of the stock solution in 50 mL of distilled water. The working solution of Compound 6 was prepared by diluting 50 mL of the stock solution in 50 mL of ethanol. The working solution of Compound 7 was prepared by diluting 25 μL of the stock solution in 50 mL of distilled water. The working solution of Compound 8 was prepared by diluting 50 μL of the stock solution in 50 mL of distilled water. Compounds 1, 2, 3, 4, 5, 6, and 8 require a 530BP+15 rm band pass filter to reduce the excitation wavelength intensity during emission measurements. Compound 7 requires the use of a 515 nm Long Pass filter (LP).

Each working solution (150 μL) was added to the test plate using an automated handling device with less than 5% error in volume measurement as in Example 1. The distilled spirits (vodka) samples were analyzed as described in Example 1.

EXAMPLE 3

Carbonated Drinks and Fruit Beverages

The analysis methods of the invention can be used in the soft drink and fruit juice industry, particularly to check third party re-formulations in every lot to monitor licensing agreements, for example. The analysis speed needed to check samples of this type should be faster than 300 samples/hour. This was not a double blind test.

Product formulations can be verified by methods similar to those described in Example 1. The fingerprint is the same when the product is produced to the same high quality of standards. Referring to Table 5, light emission was monitored in an array of six samples (Pepsi 1, Pepsi 2, Diet Pepsi 3, Coke Classic 4, Diet Coke 5, and Black Cherry 6) that were each tested four times with the four different light-emissive compounds (A, B, C, and D). Test A used compound 1. Test B used Compound 2. Test C used Compound 3. Test D used Compound 9. Each sample of the product was tested four times with each light-emissive compound.

The test methods were generally conducted in the following manner. The beverages or juices were diluted 1:10 to 1:300 with water for optimum reaction with the light emissive compounds. The optimum response of the sample is determined empirically, by using a concentration curve to maximize emission response. The sample concentration was selected to give one-half of the maximum emission response with the tested sample.

TABLE 5

| | STATISTICAL DATA | | | | HFCS/Sucrose Liquids | | | |
|---|---|---|---|---|---|---|---|---|
| | A Pepsi 1 | A Pepsi 2 | A Diet Pepsi | A Coke Classic | A Diet Coke | A Black Cherry | B Pepsi 1 | B Pepsi 2 |
| Measurement 1 | −0.8311 | −0.8360 | −0.7252 | −0.8701 | −0.6664 | −0.8449 | −0.3578 | −0.3040 |
| Measurement 2 | −0.8473 | −0.8358 | −0.7179 | −0.8716 | −0.6614 | −0.8368 | −0.3471 | −0.3294 |
| Measurement 3 | −0.8315 | −0.8349 | −0.7157 | −0.8721 | −0.6414 | −0.8432 | −0.3254 | −0.3186 |
| Measurement 4 | −0.8407 | −0.8293 | −0.7145 | −0.8633 | −0.6544 | −0.836B | −0.3368 | −0.2848 |
| Variance: | 6.105E-05 | 9.985E-06 | 2.301E-05 | 1.644E-05 | 1.179E-04 | 1.795E-05 | 1.924E-04 | 3.725E-04 |
| Mean: | −0.8376 | −0.8340 | −0.7183 | −0.8693 | −0.6559 | −0.8404 | −0.3418 | −0.3092 |
| | B Diet Pepsi | B Coke Classic | B Diet Coke | B Black Cherry | C Pepsi 1 | C Pepsi 2 | C Diet Pepsi | C Coke Classic |
| Measurement 1 | 0.3592 | −0.2481 | 0.7057 | −0.6725 | 2.3477 | 2.4311 | 3.2869 | 2.2283 |
| Measurement 2 | 0.3953 | −0.2200 | 0.7018 | −0.6583 | 2.4218 | 2.2661 | 3.2057 | 2.2739 |
| Measurement 3 | 0.3907 | −0.2192 | 0.7283 | −0.6620 | 2.4042 | 2.4579 | 3.2358 | 2.3609 |
| Measurement 4 | 0.4028 | −0.2119 | 0.7634 | −0.6731 | 2.4532 | 2.5020 | 3.3130 | 2.4228 |
| Variance: | 3.886E-04 | 2.551E-02 | 7.983E-04 | 5.589E-05 | 1.958E-03 | 1.061E-02 | 2.357E-05 | 7.589E-03 |
| Mean: | 0.3870 | −0.2248 | 0.7248 | −0.6665 | 2.4067 | 2.4143 | 3.2603 | 2.3215 |
| | C Diet Coke | C Black Cherry | D Pepsi 1 | D Pepsi 2 | D Diet Pepsi | D Coke Classic | D Diet Coke | D Black Cherry |
| Measurement 1 | 3.4794 | 1.6844 | 8.6589 | 8.8383 | 7.3358 | 8.0844 | 6.8748 | 10.4029 |
| Measurement 2 | 3.4689 | 1.6986 | 8.7641 | 9.1611 | 7.3981 | 8.3034 | 6.9779 | 10.5467 |
| Measurement 3 | 3.5929 | 1.7489 | 9.1029 | 9.1162 | 7.5821 | 8.2324 | 7.0303 | 10.5861 |
| Measurement 4 | 3.6457 | 1.9201 | 9.4517 | 9.3065 | 7.5014 | 8.6027 | 7.1879 | 11.0469 |
| Variance: | 7.507E-03 | 1.174E-02 | 0.1288 | 3.833E-02 | 1.192E-02 | 4.752E-02 | 1.705E-02 | 7.776E-02 |
| Mean: | 3.5467 | 1.7630 | 8.9944 | 9.1055 | 7.4544 | 8.3057 | 7.0177 | 10.6456 |

MSE = 0.0152267
OMEGA = 0.3232988

TABLE 6

Fingerprint Data

| | A Pepsi 1 | A Pepsi 2 | A Diet Pepsi | A Coke | A Diet Coke | A Blk Che | B Pepsi 1 | B Pepsi 2 | B Diet Pepsi | B Coke | B Diet Coke | B Blk Che |
|---|---|---|---|---|---|---|---|---|---|---|---|---|
| A Pepsi 1 | 0 | 0 | 0 | 0 | 0 | 0 | 1 | 1 | 1 | 1 | 1 | 0 |
| A Pepsi 2 | 0 | 0 | 0 | 0 | 0 | 0 | 1 | 1 | 1 | 1 | 1 | 0 |
| A Diet Pepsi | 0 | 0 | 0 | 0 | 0 | 0 | 1 | 1 | 1 | 1 | 1 | 0 |
| A Coke | 0 | 0 | 0 | 0 | 0 | 0 | 1 | 1 | 1 | 1 | 1 | 0 |
| A Diet Coke | 0 | 0 | 0 | 0 | 0 | 0 | 0 | 1 | 1 | 1 | 1 | 0 |
| A Blk Che | 0 | 0 | 0 | 0 | 0 | 0 | 1 | 1 | 1 | 1 | 1 | 0 |
| B Pepsi 1 | 1 | 1 | 1 | 1 | 1 | 1 | 0 | 0 | 1 | 1 | 1 | 1 |
| B Pepsi 2 | 1 | 1 | 1 | 1 | 1 | 1 | 0 | 0 | 1 | 1 | 1 | 1 |
| B Diet Pepsi | 1 | 1 | 1 | 1 | 1 | 1 | 1 | 1 | 0 | 1 | 1 | 1 |
| B Coke | 1 | 1 | 1 | 1 | 1 | 1 | 1 | 1 | 1 | 0 | 1 | 1 |
| B Diet Coke | 1 | 1 | 1 | 1 | 1 | 1 | 1 | 1 | 1 | 1 | 0 | 1 |
| B Blk Che | 0 | 0 | 0 | 0 | 0 | 0 | 1 | 1 | 1 | 1 | 1 | 0 |
| C Pepsi 1 | 1 | 1 | 1 | 1 | 1 | 1 | 1 | 1 | 1 | 1 | 1 | 1 |

TABLE 6-continued

| | | | | | | | | | | | |
|---|---|---|---|---|---|---|---|---|---|---|---|
| C Pepsi 2 | 1 | 1 | 1 | 1 | 1 | 1 | 1 | 1 | 1 | 1 | 1 |
| C Diet Pepsi | 1 | 1 | 1 | 1 | 1 | 1 | 1 | 1 | 1 | 1 | 1 |
| C Coke | 1 | 1 | 1 | 1 | 1 | 1 | 1 | 1 | 1 | 1 | 1 |
| C Diet Coke | 1 | 1 | 1 | 1 | 1 | 1 | 1 | 1 | 1 | 1 | 1 |
| C Blk Che | 1 | 1 | 1 | 1 | 1 | 1 | 1 | 1 | 1 | 1 | 1 |
| D Pepsi 1 | 1 | 1 | 1 | 1 | 1 | 1 | 1 | 1 | 1 | 1 | 1 |
| D Pepsi 2 | 1 | 1 | 1 | 1 | 1 | 1 | 1 | 1 | 1 | 1 | 1 |
| D Diet Pepsi | 1 | 1 | 1 | 1 | 1 | 1 | 1 | 1 | 1 | 1 | 1 |
| D Coke | 1 | 1 | 1 | 1 | 1 | 1 | 1 | 1 | 1 | 1 | 1 |
| D Diet Coke | 1 | 1 | 1 | 1 | 1 | 1 | 1 | 1 | 1 | 1 | 1 |
| D. Blk Che | 1 | 1 | 1 | 1 | 1 | 1 | 1 | 1 | 1 | 1 | 1 |

HFCS/Sucrose Liquids

| | C Pepsi 1 | C Pepsi 2 | C Diet Pepsi | C Coke | C Diet Coke | C Blk Che | D Pepsi 1 | D Pepsi 2 | D Diet Pepsi | D Coke | Diet Coke | D Blk Che |
|---|---|---|---|---|---|---|---|---|---|---|---|---|
| A Pepsi 1 | 1 | 1 | 1 | 1 | 1 | 1 | 1 | 1 | 1 | 1 | 1 | 1 |
| A Pepsi 2 | 1 | 1 | 1 | 1 | 1 | 1 | 1 | 1 | 1 | 1 | 1 | 1 |
| A Diet Pepsi | 1 | 1 | 1 | 1 | 1 | 1 | 1 | 1 | 1 | 1 | 1 | 1 |
| A Coke | 1 | 1 | 1 | 1 | 1 | 1 | 1 | 1 | 1 | 1 | 1 | 1 |
| A Diet Coke | 1 | 1 | 1 | 1 | 1 | 1 | 1 | 1 | 1 | 1 | 1 | 1 |
| A Blk Che | 1 | 1 | 1 | 1 | 1 | 1 | 1 | 1 | 1 | 1 | 1 | 1 |
| B Pepsi 1 | 1 | 1 | 1 | 1 | 1 | 1 | 1 | 1 | 1 | 1 | 1 | 1 |
| B Pepsi 2 | 1 | 1 | 1 | 1 | 1 | 1 | 1 | 1 | 1 | 1 | 1 | 1 |
| B Diet Pepsi | 1 | 1 | 1 | 1 | 1 | 1 | 1 | 1 | 1 | 1 | 1 | 1 |
| B Coke | 1 | 1 | 1 | 1 | 1 | 1 | 1 | 1 | 1 | 1 | 1 | 1 |
| B Diet Coke | 1 | 1 | 1 | 1 | 1 | 1 | 1 | 1 | 1 | 1 | 1 | 1 |
| B Blk Che | 1 | 1 | 1 | 1 | 1 | 1 | 1 | 1 | 1 | 1 | 1 | 1 |
| C Pepsi 1 | 0 | 0 | 1 | 0 | 1 | 1 | 1 | 1 | 1 | 1 | 1 | 1 |
| C Pepsi 2 | 0 | 0 | 1 | 0 | 1 | 1 | 1 | 1 | 1 | 1 | 1 | 1 |
| C Diet Pepsi | 1 | 1 | 0 | 1 | 0 | 1 | 1 | 1 | 1 | 1 | 1 | 1 |
| C Coke | 0 | 0 | 1 | 0 | 1 | 1 | 1 | 1 | 1 | 1 | 1 | 1 |
| C Diet Coke | 1 | 1 | 0 | 1 | 0 | 1 | 1 | 1 | 1 | 1 | 1 | 1 |
| C Blk Che | 1 | 1 | 1 | 1 | 1 | 0 | 1 | 1 | 1 | 1 | 1 | 1 |
| D Pepsi 1 | 1 | 1 | 1 | 1 | 1 | 1 | 0 | 0 | 1 | 1 | 1 | 1 |
| D Pepsi 2 | 1 | 1 | 1 | 1 | 1 | 1 | 0 | 0 | 1 | 1 | 1 | 1 |
| D Diet Pepsi | 1 | 1 | 1 | 1 | 1 | 1 | 1 | 1 | 0 | 1 | 1 | 1 |
| D Coke | 1 | 1 | 1 | 1 | 1 | 1 | 1 | 1 | 1 | 0 | 1 | 1 |
| D Diet Coke | 1 | 1 | 1 | 1 | 1 | 1 | 1 | 1 | 1 | 1 | 0 | 1 |
| D Blk Che | 1 | 1 | 1 | 1 | 1 | 1 | 1 | 1 | 1 | 1 | 1 | 0 |

Stock solutions of the light-emissive compounds were prepared by dissolving Compound 1 at a concentration of 1.5 mM in 1:2 DMSO/water, Compound 2 at a concentration of 2 mM in DMSO, Compound 3 at a concentration of 1 mM in DMSO, and Compound 9 at a concentration of 10 mM in DMSO.

The concentrations of working solutions of light emissive compounds were optimized as described in Example 1. Optimum concentrations were calculated from the concentrations of light-emissive compound that provide emission intensity values that can discriminate a standard product sample from other the unknown samples by a value greater than omega. The working solution of Compound 1 was prepared by diluting 75 µL of the stock solution in 50 mL of distilled water. The working solution of Compound 2 was prepared by diluting 120 µL of the stock solution in 20 mL of distilled water. The working solution of compound 3 was prepared by diluting 100 µL of the stock solution in 20 mL of distilled water. The working solution of Compound 9 was prepared by diluting 50 µL of the stock solution in 50 mL of distilled water.

Compounds 1, 2, 3, and 9 require a 530BP±15 nm band pass filter to reduce the excitation wavelength intensity during the emission measurements. The sample placement and emission analysis was carried out as described in Example 1. The results of the experiment are presented in Table 5. There were four different measurements (A, B, C, and D) made for each sample in combination with each light-emissive compound. Each measurement was repeated four times to demonstrate the level of reproducibility. Variance and mean were calculated for each group of 4 measurements. The 95% confidence levels were used for this fingerprint analysis. If two sample means differ by an amount greater than omega, the samples are different (i.e. substantially similar in composition). For example, in the test with light-emissive compound D, sample Pepsi 1 had a mean light emission of 8.9944 and sample Pepsi 2 had a mean light emission of 9.1055. The difference in light emission was 0.1111. The omega for the test was 0.3232988. If the difference (0.1111) is greater than omega for any two samples, then the samples are substantially the same. Therefore, Pepsi 1 and Pepsi 2 are substantially the same.

The fingerprint data are presented in Table 6 to make all possible comparisons and are established in the same manner as in Example 1. As a result of the fingerprinting analysis in Table 6, Pepsi 1 and Pepsi 2 are pairs, with similar compositions, and the other samples are not related.

EXAMPLE 4

One-Step Analysis of Beverages

The methods of Example 3 can be modified to monitor key ingredients in beverages. Importantly, it was discovered that the key ingredients that are currently measured by standard analytical methods for authenticity monitoring can also be measured by the methods of automated emission measurements of the invention. In other words, there are some ingredients inherent to certain products that have characteristic light-emission properties. The methods can be used to analyze these components in a single-plate analysis with the all the light-emissive compounds combined together, thereby allowing modification and automation of the method into a simple, one-step inexpensive emission scan.

Standard ingredients that are monitored in colas are, for example, high fructose corn syrup (HFCS)I caffeine, potassium benzoate, sodium benzoate, pH, and aspartame. Two combinations of light-emissive Compounds have been developed for the analysis of colas. Combination 1 allows monitoring of sugar (or HFCS) sources, caffeine, pH, and preservatives (such as potassium or sodium benzoate). combination 1 is useful for analyzing ordinary carbonated beverages. Combination 2 is tailored for the analysis of diet carbonated beverages and allows monitoring of aspartame, caffeine, pH, and preservatives. The Combinations are designed to detect changes in specific ingredients from at 0.1, 0.3, 0.5, 1, 2, and 3 percent reduction levels.

Combination 1 includes Compound 1, Compound 3, and Compound 11 for the analysis of sugar (or HFCS). Caffeine is a light-emissive compound alone and does not require addition of another component to the mixture. The common preservatives, potassium and sodium benzoate, can be identified using a number of light-emissive compounds. For example, Compound 12 is a potassium sensitive dye. The carboxylic acid on the benzoate group is reactive with all alkyl halide, carbodimide, and alcohol containing light-emissive compounds (see Table 1). The pH can be determined using any pH-sensitive light-emissive compound that emits in range from of pH from 1–4 (most soft drinks range in pH from 2.4–4.0). A specific example of a pH-sensitive light emissive compound is Compound 13.

Stock solutions of the light-emissive compounds were prepared by dissolving Compound 1 at a concentration of 1.5 mM in a 1:1 DMSO/water mixture, Compound 3 at a concentration of 0.5 mM in 1:1 mixture of DMSO/water, Compound 11 at a concentration of 10 mM in ethanol, Compound 12 at a concentration of 10 mM in DMSO, and Compound 13 at a concentration of 10 mM in distilled water.

The working concentrations were optimized for identification of key ingredients for each soft drink beverage product, as described in Example 1. The working solution of Compound 1 was prepared by diluting 75 μL of the stock solution in 50 mL of distilled water. The working solution of Compound 3 was prepared by diluting 100 μL of the stock solution in 20 mL of water. The working solution of Compound 11 was prepared by diluting 50 μL of the stock solution in 50 mL of distilled water. The working solution of Compound 12 was prepared by diluting 50 μL of the stock solution in 50 mL of distilled water. The working solution of Compound 13 was prepared by diluting 50 μL in 100 mL of distilled water.

Caffeine (anhydrous; Sigma Reference Standard Product IC-1778) was used as a standard in a caffeine-free beverage (product specific) as an internal calibration standard for the presence of caffeine. Caffeine has excitation maxima at 254 nm and 330 nm and an emission maximum at 350 nm.

Compound 1 and Compound 3 both require a 520BP±15 nm band pass filter. Caffeine requires a 345LP nm long pass filter. Compound 11 requires a 365B+15 band pass filter. Compound 12 requires a 460BP+6.8 nm band pass filter. Compound 13 requires a 550BP+15 nm band pass filter.

Combination 2, for analyzing diet carbonated beverages is essentially the same as Combination I except that Compounds 1, 3, and 11 are replaced by light-emissive compounds that indicate the relative presence of aspartame. These include light-emissive compounds that react, or interact, with carboxylic acid groups and amine groups. See Table 1 for examples.

EXAMPLE 5

Infant Formulas

The methods of the invention can be used in the infant formula industry as for product authentication. In 1995, a counterfeit-labeled version of infant formula was illegally distributed to grocery chains in 16 states. Authenticating infant formula on shelves can help assure formula customers that a product is authentic and reliable, Using the methods, one can insure that the product at the source matches the product at the destination. In addition, it can be possible to detect product tampering by, fingerprint analysis.

Product formulations can be verified by methods similar to those described in Example 1. The fingerprint is the same when the product is produced to the same high quality of standards. Referring to Table 7, light emission was monitored in an array of six samples (Gerber, Similac liquid, Similac powder, Carnation Follow-Up, Enfamil, and a powdered milk standard) that were each tested four times with a light-emissive compound. The light-emissive compound included Compound 1, Compound 2, Compound 3, and Compound 7.

The samples were prepared by diluting the infant formulas with distilled water according to manufacturer instructions (e.g., 8.5 grams in 60 mL of distilled water). The resulting solutions were further diluted by a factor of 1000, and filtered using a Millipore 0.22/μm sterile syringe filter. The filter samples were used directly in the analyses.

Stock solutions of the light-emissive compounds were prepared that contained Compound 1 at a concentration of 1.5 mM in a 1:2 DMSO/water mixture, Compound 2 at a concentration of 2 mM in DMSO, Compound 3 at a concentration of 1 mM in DMSO, and Compound 7 at a concentration of 1 mM in distilled water.

Working solution concentrations were determined as described in Example 1. The working solution of Compound 1 was prepared by diluting 75 μL of the stock solution in 20 mL of distilled water. The working solution of Compound 2 was prepared by diluting 120 μL of the stock solution in 20 mL of distilled water. The working solution of Compound 3 was prepared by diluting 100 μL of the stock solution in 20 mL of distilled water. The working solution of Compound 7 was prepared by diluting 25 μL of the stock solution in 50 mL of distilled water.

Compounds 1, 2, 3, and 7 require a 530BP±15 nm band pass filter to reduce the excitation wavelength intensity in the emission measurement. The analysis was conducted as described in Example 1. The diluted and filtered samples were added directly to the dyes and the emission measured.

The results of the experiment are presented in Table 7. There was one measurement made for each sample in combination with the light-emissive compound. Each measurement was repeated four times to demonstrate the level of reproducibility. Variance and mean were calculated for each group of 4 measurements. The 95% confidence levels were used for this fingerprint analysis. The analysis is similar to that described in Examples 1 and 2.

For example, the Gerber sample had a mean light emission of −0.2049 and the Similac sample had a mean light emission of −0.1941. The difference in light emission was 0.0108. The omega for the test was 0.044. If the difference (0.0108) is less than omega for any two samples, then the samples are substantially the same. Therefore, the products are substantially the same. The fingerprint data are presented in Table 8 to make all possible comparisons and are established in the same manner as in Example 1. As a result of the fingerprinting analysis in Table 8, the Gerber, Similac and Enfamil samples are the same. However, the Carnation and Standard are different. The Standard is Carnation Evaporated Milk.

TABLE 7

|  | Gerber | Similac Lq | Similac Pw | Carnation | Enfamil | Standard |
|---|---|---|---|---|---|---|
| Meas. 1 | −0.2022 | −0.1912 | −0.2109 | −0.3088 | −0.2143 | −0.1022 |
| Meas. 2 | −0.2025 | −0.2061 | −0.2102 | −0.3196 | −0.1511 | −0.1154 |
| Meas. 3 | −0.1988 | −0.1814 | −0.2410 | −0.3037 | −0.2493 | −0.1094 |
| Meas. 4 | −0.2159 | −0.1979 | −0.1926 | −0.3162 | −0.2005 | −0.1155 |
| Variance | 5.708E-05 | 0.0001094 | 0.0004035 | 5.163E-05 | 0.0016566 | 3.968E-05 |
| Mean | −0.2049 | −0.1942 | −0.2137 | −0.3121 | −0.2038 | −0.1106 |

MSE = 0.0195
OMEGA = 0.044

TABLE 8

|  | Gerber | Similac Lq | Similac Pw | Carnation | Enfamil | Standard |
|---|---|---|---|---|---|---|
| Gerber | 0 | 0 | 0 | 1 | 0 | 1 |
| Similac Lq | 0 | 0 | 0 | 1 | 0 | 1 |
| Similac Pw | 0 | 0 | 0 | 1 | 0 | 1 |
| Carnation | 1 | 1 | 1 | 0 | 1 | 0 |
| Enfamil | 0 | 0 | 0 | 1 | 0 | 1 |
| Standard | 1 | 1 | 0 | 1 | 0 | 0 |

EXAMPLE 6

Vanilla Extract

The Federation of Extracts Manufacturing Association needs to determine origin of vanilla extract. The technology of the present invention was used to identify geographical origin of vanilla samples. To date there was not a practical method for identifying geographical origin of vanillas. Geographical origin can be verified by methods similar to those described in Example 1. The fingerprint of a Vanilla extract is the same when the sample comes from the same geographical region. Referring to the table entitled FEMA Vanilla Extracts Pilot Program #1, Vanilla prized as high value from Bourbon had a fluorescent value ranging from 0.57–7.76. In contrast, vanilla from Java, a lessor valued extract, had a fluorescent value ranging from 9.42–13.57. The test methods were generally conducted in the following manor. The vanilla extracts were diluted 1/20 with water for optimum reaction with the light emissive compounds. The optimum response of the vanilla sample is determined empirically, by using a concentration curve to maximize infrared region emission response. Stock solutions of the light-emissive compounds were prepared by dissolving Indocyanine green at a concentration of 1.5 mM in 1:2 DMSO/water right before use and are only good for approximately 2 hours kept at room temperature. The working solution of this compound was prepared by diluting 120 $\mu$l of the stock in 20 ml of distilled water. Indocyanine green has an excitation wavelength of 775 nm. The sample placement and emission analysis was carried out as described in Example 1. The result of the experiment are presented in table 9. There were four measurements of the vanilla samples in each geographical region made for each combination with each light emissive compound. If two geographical regions differ by an amount greater than Omega, then the vanilla from the regions can be distinguished. The Omega for the Indocyanine green dye #1, is 0.35 and therefore Bourbon can be distinguished from Java.

TABLE 9

FEMA VANILLA EXTRACT PILOT PROGRAM
VANILLA DYE #1
Developed for FEMA

| Sample | GFM | Sample | GFM | Sample | GFM | Sample | GFM |
|---|---|---|---|---|---|---|---|
| Bourbon #1 | 0.57 | | | | | | |
| Bourbon #21 | 2.48 | | | | | | |
| | | Madagascar #18 | 1.94 | | | | |
| | | Madagascar #19 | 3.90 | | | | |
| | | Madagascar #24 | 4.54 | | | | |
| | | Madagascar #26 | 5.30 | | | | |

TABLE 9-continued

FEMA VANILLA EXTRACT PILOT PROGRAM
VANILLA DYE #1
Developed for FEMA

| Sample | GFM | Sample | GFM | Sample | GFM |
|---|---|---|---|---|---|
| | | Comoros #27 | 4.09 | | |
| Bourbon #40 | | Comoros #11 | 5.60 | | |
| | | Comoros #12 | 5.89 | | |
| | | Tonga #30 | 5.27 | | |
| | | Tonga #16 | 6.50 | | |
| | | Indonesian #17 | 5.50 | | |
| | | Indonesian #20 | 8.34 | | |
| | | Bali #29 | 7.96 | | |
| | | Bali #36 | 9.43 | | |
| | | | | Java #13 | 9.42 |
| | | | | Java #38 | 10.33 |
| | | | | Java #14 | 10.66 |
| | | | | Java #6 | 13.57 |
| | | | | OMEGA | 0.35 |

Note: #s Refer to FEMA Code

EXAMPLE 7

In this example, light emissive compounds 1 & 4 were used to identify a patented compound. A product from China has the same light emissive fingerprint. The chances of this happening due to chance alone for 4 replicates repeated 1 time is 1:100, repeated two times 1:10,000 and repeated three times is 1:1,000,000. Therefore these compositions have both the same compound and the same concentration of the compound in the formulation. It also can be inferred that the compounds were manufactured by the same process. In this example the product was diluted 1:1000 w/w and filtered with a 0.22 μm filter to remove particles. Compound 1 and compound 4 were prepared as described previously. The results of this experiment are presented in tables 10 and 11, below. There were four measurements made of the customer's compound (Std#39). The Chinese products #7 and #10 had the same measurements as the standard, sample #39. The patented compound has the same emissive response with dye 1 as the two "suspect formulation" i.e. 81.9 not different from 79.6 or 79.7 with an omega of 3.2. Measuring using another dye, the same emissive response as the two "suspect formulations" i.e. 23.97 is not different from 24.86 and 24.40 with an omega of 1.58.

TABLE 10

STATISTICAL DATA: Dye 1

| | Std #39 | Chinese #7 | Chinese #10 |
|---|---|---|---|
| Measurement 1 | 81.3 | 80.3 | 77.1 |
| Measurement 2 | 81.0 | 79.1 | 80.7 |
| Measurement 3 | 82.5 | 79.2 | 80.2 |
| Measurement 4 | 82.7 | 79.9 | 80.7 |
| Variance | 0.6797 | 0.3068 | 3.1052 |
| Mean | 81.9 | 79.6 | 79.7 |
| MSE | 0.1364 | | |
| OMEGA | 3.2 | | |

TABLE 11

STATISTICAL DATA: Dye 4

| | FF w/Std #39 | FF w/Chinese #7 | FF w/Chinese #10 |
|---|---|---|---|
| Measurement 1 | 24.21 | 24.84 | 24.36 |
| Measurement 2 | 25.14 | 25.12 | 23.98 |
| Measurement 3 | 23.54 | 24.74 | 24.38 |
| Measurement 4 | 22.99 | 24.73 | 24.86 |
| Variance | 0.09 | 0.00 | 0.01 |
| Mean | 23.97 | 24.86 | 24.40 |
| MSE | 0.03 | 0.00 | 0.00 |
| OMEGA | 1.58 | 0.00 | 0.00 |

Other embodiments are within the claims:

What is claimed is:

1. A method for determining relatedness of a sample to a standard known to be authentic or known to have at least one selected characteristic of authentic material, the method comprising:
   a. providing a sample product which is free of any exogenous product tag;
   b. providing a test sample comprising the sample product and at least one light-emissive compound;
   c. irradiating the test sample with an irradiating wavelength of light;
   d. monitoring at least one emitted wavelength of light, generated in response to the irradiating wavelength of light, to establish a sample emission profile;
   e. providing a standard fingerprint characteristic of a standard, the standard comprising the standard and the light-emissive compound and the standard fingerprint being generated by irradiating several of the standard with the irradiating wavelength and monitoring the emitted wavelength in response thereto; and
   f. comparing the sample emission profile with the standard fingerprint to determine whether the sample is authentic.

2. The method of claim 1 further comprising:
   providing a background control which comprises the light-emissive compound without the sample or the standard;
   irradiating the background control with the irradiating wavelength and monitoring the emitted wavelength in response thereto, to establish background emission; and determining the emission profile of the sample based on at least one difference between the emission of the control and the emission of the test sample.

3. The method of claim 1 in which the light-emissive compound is added to the sample by an automated pipette.

4. The method of claim 1, wherein the sample mixture is dispensed by an automated pipette in a multiwell plate.

5. The method of claim 1, wherein the standard, the sample, or both inherently include a fluorescent, phosphorescent, or luminescent compound.

6. The method of claim 5 in wherein the compound is caffeine.

7. The method of claim 1, wherein the light-emissive compound is fluorescent, phosphorescent, or luminescent.

8. The method of claim 1 in which the light-emissive compound reacts with components of the sample or the standard or both to yield at least one fluorescent, phosphorescent, or luminescent component.

9. A method for determining whether a product is authentic, comprising:

obtaining a liquid sample of a product which is free of any exogenous product tag, and then combining with the liquid sample a light emissive compound which interacts with an analyte of the product to form a test sample, irradiating the test sample, determining the intensity of light emitted from the test sample at a wave length, and comparing the intensity of light emitted from the test sample to the intensity of light emitted as a result of irradiating a mixture of the light emissive compound and an authentic liquid standard of the product, wherein similarity of light emission intensity is determinative of authenticity of the sample and dissimilarity of light emission intensity is determinative of nonauthenticity of the sample.

10. The method of claim 9, wherein the chemical composition of the product is unknown.

11. The method of claim 9, wherein the chemical structure of the analyte to which the light emissive compound binds is assumed.

12. The method of claim 9, wherein the product is a liquid consumable product.

13. The method of claim 9, wherein said light emissive compound is a plurality of light emissive compounds and said analyte is a plurality of analytes, each light emissive compound binding to a different of said analytes.

14. The method of claim 9, wherein said light emissive compound is a plurality of light emissive compounds, wherein said plurality of light emissive compounds is between 3 and 7 compounds.

15. The method of claim 9, wherein the intensity of light emitted from the test sample is compared to the intensity of light emitted from a plurality of said mixture, and wherein authenticity requires the intensity of light emitted from the test sample to be within a pre-selected confidence limit defining a range of intensity calculated from the intensity of light emitted from the plurality of said mixture.

16. The method of claim 9, wherein said comparing the intensity of light is computer-implemented.

* * * * *